(12) United States Patent
Gorans et al.

(10) Patent No.: US 11,963,717 B2
(45) Date of Patent: Apr. 23, 2024

(54) ENERGY DELIVERY SYSTEM USING AN ELECTRIC FIELD

(71) Applicant: Nova-Tech Engineering, LLC, Willmar, MN (US)

(72) Inventors: Marc S. Gorans, Sturgis, SD (US); James J. Kleven, Willmar, MN (US); Wade D. Werder, Sunburg, MN (US); Jacob R. French, Willmar, MN (US); Derek Worcester, Willmar, MN (US)

(73) Assignee: Nova-Tech Engineering, LLC, Willmar, MN (US)

( * ) Notice: Subject to any disclaimer, the term of this patent is extended or adjusted under 35 U.S.C. 154(b) by 714 days.

(21) Appl. No.: 17/057,399

(22) PCT Filed: Jun. 7, 2019

(86) PCT No.: PCT/US2019/035988
§ 371 (c)(1),
(2) Date: Nov. 20, 2020

(87) PCT Pub. No.: WO2019/236964
PCT Pub. Date: Dec. 12, 2019

(65) Prior Publication Data
US 2021/0259768 A1 Aug. 26, 2021

Related U.S. Application Data

(60) Provisional application No. 62/682,262, filed on Jun. 8, 2018.

(51) Int. Cl.
*A61N 5/04* (2006.01)
*A61B 18/00* (2006.01)
(Continued)

(52) U.S. Cl.
CPC .......... *A61B 18/1815* (2013.01); *A61D 1/005* (2013.01); *A61N 5/04* (2013.01);
(Continued)

(58) Field of Classification Search
CPC ...... A61B 18/1815; A61B 2018/00601; A61B 2018/00642; A61B 2018/00666;
(Continued)

(56) References Cited

U.S. PATENT DOCUMENTS 4,237,891 A 12/1980 Dubose
5,195,925 A 3/1993 Gorans
(Continued)

FOREIGN PATENT DOCUMENTS

EP 2 168 520 3/2010
FR 1 309 191 11/1962
(Continued)

OTHER PUBLICATIONS

Examination Report issued in India for Application No. 202017052628 dated Sep. 30, 2022 (6 pages). English translation included.
(Continued)

*Primary Examiner* — Khadijeh A Vahdat
(74) *Attorney, Agent, or Firm* — Mueting Raasch Group

(57) ABSTRACT

An energy delivery system includes an RF synthesizer circuit configured to generate an RF electric signal and a preamplification stage operably coupled to the RF synthesizer circuit. The preamplification stage has at least one attenuator. A board controller is operably coupled to the attenuator of the preamplification stage that is configured to modify a gain setting of the attenuator. An output connection is configured to provide a low-power signal or a high-power signal based on at least the RF electric signal and the gain setting. The low-power signal or high-power signal is provided to an RF applicator configured to couple an alternating RF electric field to animal tissue.

29 Claims, 13 Drawing Sheets

(51) Int. Cl.
*A61B 18/18* (2006.01)
*A61D 1/00* (2006.01)

(52) U.S. Cl.
CPC ............... *A61B 2018/00642* (2013.01); *A61B 2018/00678* (2013.01); *A61B 2018/00702* (2013.01); *A61B 2018/00732* (2013.01); *A61B 2018/00755* (2013.01); *A61B 2018/00785* (2013.01); *A61B 2018/00904* (2013.01); *A61B 2018/1823* (2013.01); *A61B 2018/1876* (2013.01)

(58) Field of Classification Search
CPC .......... A61B 2018/00678; A61B 2018/00702; A61B 2018/00732; A61B 2018/00755; A61B 2018/00761; A61B 2018/00779; A61B 2018/00785; A61B 2018/00845; A61B 2018/00875; A61B 2018/00904; A61B 2018/1823; A61B 2018/1876; A61B 2034/715
See application file for complete search history.

(56) References Cited

U.S. PATENT DOCUMENTS

| | | |
|---|---|---|
| 5,540,681 A | 7/1996 | Strul |
| 5,651,731 A | 7/1997 | Gorans |
| 5,906,613 A | 5/1999 | Mulier |
| 7,232,450 B2 | 6/2007 | Gorans |
| 8,469,954 B2 | 6/2013 | Young |
| 9,775,695 B2 | 10/2017 | Erickson |
| 2013/0267943 A1* | 10/2013 | Hancock ............... H05B 6/806 606/33 |

FOREIGN PATENT DOCUMENTS

| | | |
|---|---|---|
| GB | 2 457 604 | 8/2010 |
| WO | WO 92/13459 | 8/1992 |
| WO | WO 2014/184544 | 11/2014 |

OTHER PUBLICATIONS

PCT Search Report and Written Opinion for PCT/US2019/035988 dated Sep. 10, 2019 (17 pages).
PCT International Preliminary Report on Patentability for PCT/US2019/035988 dated Oct. 23, 2020 (20 pages).
RFEM24-250: 2.45 GHz RF Energy Module, 3 pages. https://www.nxp.com/products/rf/rf-power/rf-cooking/2450-mhz-subsystem-for-rf-cooking/2.45-ghz-rf-energy-module:RFEM24-250.
RFEL24-500 NXP RF Energy Lab Box, Jun. 2018, 2 pages.
RFEM24-250 2.45 GHz RF Energy Module, Jun. 2018, 2 pages. https://www.mouser.com/datasheet/2/302/RFEM24-250FS-1370622.pdf.
RF Energy Module Interface Reference Manual, Oct. 2018, 30 pages.

* cited by examiner

ENERGY DELIVERY SYSTEM USING AN ELECTRIC FIELD

The present application is a § 371 U.S. National Stage of International Application No. PCT/US2019/035988 filed 7 Jun. 2019, which claims the benefit under 35 U.S.C. § 119 of U.S. Provisional Application Ser. No. 62/682,262, filed Jun. 8, 2018, which disclosures are incorporated by reference herein in their entireties.

The present disclosure relates to energy delivery systems. In particular, the present disclosure relates to energy delivery systems that generate electric fields for processing animal tissue.

The processing of poultry may include activities such as sexing to determine gender, inoculating, or otherwise medicating the birds, feeding the birds, weighing the birds, and processing the beaks and/or claws of the birds, for example, to retard their growth, among other activities.

In recent years, some systems have delivered energy to selected poultry tissue for purposes of processing. U.S. Pat. Nos. 5,195,925; 5,651,731; 7,232,450; and 9,775,695 describe some systems and methods for processing beaks and claws of poultry that are more welfare friendly methods to the bird. There remains a need for improved energy delivery systems that even more precisely deliver energy.

SUMMARY

Various aspects of the present disclosure relate to a system that uses an electric field to process animal tissue. The design of the system includes an attenuator operably coupled between a radio frequency (RF) synthesizer and at least one amplifier to provide a precise and dynamic power gain control of an RF electric signal over a wide range, for example, up to 60 dB to generate an alternating RF electric field. In particular, the attenuator may be adjusted without adjusting some or all amplifiers. The system may selectively provide a low- or high-power alternating RF electric field. The system may have an RF interface board designed to isolate sensing circuitry from high-power signals. The system may be used in various applications, such as the processing of poultry claws, beaks/bills, etc. Processing may be accomplished using one or more non-contact energy sources, such as an electric field. Processing may include delivery of energy to selected tissue in amounts sufficient to retard, or slow, future growth but not directly remove the tissue. Processing may also include delivery of energy to selected tissue in amounts sufficient to remove the tissue.

In one aspect, an energy delivery system comprises an RF synthesizer circuit configured to generate an RF electric signal. The system also comprises a preamplification stage operably coupled to an output of the RF synthesizer circuit. The preamplification stage comprises an attenuator. The system also comprises a board controller operably coupled to the attenuator of the preamplification stage. The board controller is configured to modify a gain setting of the attenuator. The system further comprises an output connection configured to provide a low-power signal or a high-power signal based on at least the RF electric signal and the gain setting of the attenuator. The low-power signal or the high-power signal is configured to be provided to an RF applicator configured to couple an alternating RF electric field to animal tissue.

In another aspect, a method of delivering energy to animal tissue comprises synthesizing an RF electric signal; adjusting attenuation of the RF electric signal to selectively provide a low-power signal or a high-power signal; and generating an alternating RF electric field from an RF applicator based on the low-power signal or the high-power signal to couple the alternating RF electric field to animal tissue.

BRIEF DESCRIPTION OF THE DRAWINGS

Various embodiments of the present disclosure are described in detail herein with respect to the following drawings.

DETAILED DESCRIPTION

Figure 1:
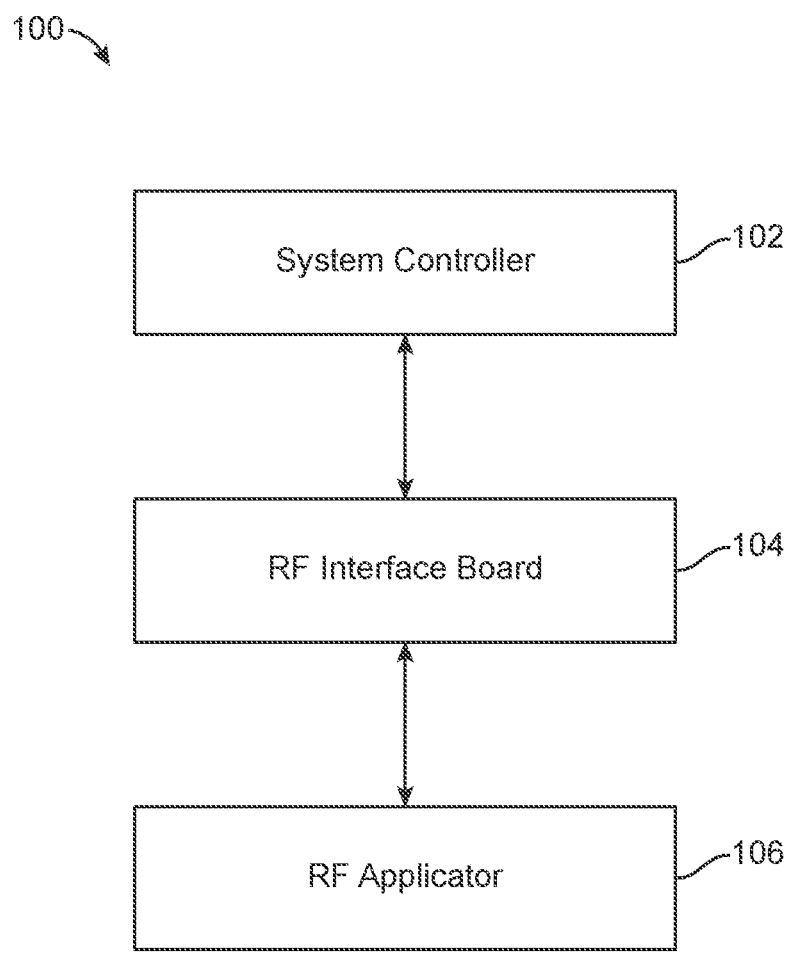
FIG. 1 illustrates an energy delivery system of the present disclosure.

This disclosure relates to energy delivery systems and, in particular, to energy delivery systems that use one or more non-contact energy sources, such as electric fields, that couple to animal tissue. Although reference is made herein to poultry systems, such as a poultry claw system used to deliver energy to each claw in amounts sufficient to retard claw growth but not directly remove the claw, the energy delivery systems may be used with any poultry, or other animal, tissue, for which processing may be desirable (e.g., beak/bill tissue of poultry, etc.). Processing may also include delivery of energy to selected tissue in amounts sufficient to remove tissue. Various other applications for energy delivery systems will become apparent to one of ordinary skill in the art having the benefit of the present disclosure.

It may be beneficial to provide an energy delivery system having precise and dynamic control over a wide range of power gains to provide alternating radio frequency (RF) electric fields, particularly in tissue processing systems for animals. It may be beneficial to provide an energy delivery system capable of providing a low- or high-power RF electric field to facilitate detecting and processing of animal tissue using the same system. Further, it may be beneficial for the energy delivery system to control the RF electric field precisely to provide targeted energy to the animal tissue to achieve the desired processing while mitigating undesirable effects.

The present disclosure provides a system that uses an electromagnetic field to process animal tissue. The system may be used in poultry processing for stunting the growth of poultry claws. The system may selectively provide a low- or high-power alternating RF electric field. The low-power alternating RF electric field may be used for sensing the presence of animal tissue. The high-power alternating RF electric field may be used for processing the animal tissue. Some commercially-available high-power RF amplifiers are not capable of precise dynamic gain control at low gains. Advantageously, in various embodiments of the present disclosure, one or more preamplification stages may be used to provide precise, dynamic attenuation or amplification over a wide range of power gains. In some embodiments, the preamplification stage paired with one or more amplification stages may provide a wide range of dynamic gain control range, for example, up to 60 dB for an RF electric signal that can be used to provide an alternating RF electric field.

In some embodiments, attenuators are adjusted instead of adjusting amplifiers to provide the dynamic gain range. Frequency tracking may be used in conjunction with the high-power alternating RF electric field to improve coupling to animal tissue while processing. Further, in some embodiments, the system may have an RF interface board designed to isolate sensing circuitry to facilitate power sensing when providing either low- or high-power output RF electric signals.

All scientific and technical terms used herein have meanings commonly used in the art unless otherwise specified. The definitions provided herein are to facilitate understanding of certain terms used frequently herein and are not meant to limit the scope of the present disclosure.

As used herein, the term "animal tissue" refers non-human tissue. Non-limiting examples of animal tissue include a poultry claw, beak/bill, or other appendage.

As used herein, the term "applicator" or "RF applicator" refers to a structure configured to provide an alternating RF electric field in response to receiving an RF electric signal. The applicator is configured to couple alternating RF electric field energy into animal tissue. In contrast to an RF antenna, an RF applicator directs, or concentrates, alternating RF electric field energy locally at a point proximate to, or within a close proximity to, the surface of the structure instead of transmitting the RF electric field to a receiving antenna across a medium.

As used herein, the term "or" is generally employed in its inclusive sense, for example, to mean "and/or" unless the context clearly dictates otherwise. The term "and/or" means one or all the listed elements or a combination of at least two of the listed elements.

Reference will now be made to the drawings, which depict one or more aspects described in this disclosure. However, it will be understood that other aspects not depicted in the drawings fall within the scope of this disclosure. Like numbers used in the figures refer to like components, steps, and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

FIG. 1 shows energy delivery system 100 according to the present disclosure. System 100 includes one or more of components, such as system controller 102, RF interface board 104, and RF applicator 106.

System controller 102 may be operably connected to RF interface board 104 to provide, or issue, commands and settings to RF interface board 104. RF interface board 104 may use a calibration or compensation table to correct for signal drift due to changes in frequency or temperature affecting one or more components of RF interface board 104.

RF interface board 104 may be configured to generate an RF electric signal. The RF electric signal may be amplified or attenuated by various components of RF interface board 104 to produce an output RF electric signal. In some embodiments, RF interface board 104 includes at least an RF synthesizer circuit, an attenuator, an amplifier, a sensing circuit, and an output connection to provide the output RF electric signal. The RF interface board 104 is configured to provide a low- or high-power output RF electric signal based the generated RF electric signal. RF interface board 104 may include one or more: additional attenuators, additional amplifiers, temperature sensors, and electromagnetic shielding components.

RF applicator 106 may be operably connected to RF interface board 104 to generate an alternating RF electric field in response to receiving the output RF electric signal. RF applicator 106 may be operably connected to the output connection of RF interface board 104. RF applicator 106 may be formed of any suitable structure capable of producing, or transmitting, an alternating RF electric field. In some embodiments, RF applicator 106 includes a conductive material and a dielectric material. For example, RF applicator 106 may include two conductors separated by a dielectric material. Non-limiting examples of the dielectric material include a polymer, such as polytetrafluoroethylene (PTFE), such as TEFLON, or a free-space dielectric (air).

RF interface board 104 is configured to carry out, or execute, one or more commands provided by system controller 102. In some embodiments, RF interface board 104 is configured to receive commands including one or more of: a constant power output command, a detection mode command, a high-power tracking mode command, an error reporting command, a temperature sensing command, a shutdown command, and a turn on command.

Various commands may be used during operation of the energy delivery system. In response to the constant power output command, RF interface board 104 may provide a constant power RF electric signal to the output connection. For example, the constant power may correspond to a low- or high-power output RF electric signal. In response to the detection mode, RF interface board 104 may be configured to detect a change in return loss of the low-power signal. Further, RF interface board 104 may notify system controller 102 when the reflected power drops below, or return loss rises above, a threshold value. The detection mode may be used in conjunction with providing the low-power output RF electric signal to RF applicator 106. When detected return loss rises, animal tissue may be positioned in close proximity to RF applicator 106, and system controller 102 may command RF interface board 104 to provide a high-power output RF electric signal. In response to the high-power tracking mode, RF interface board 104 may modify the frequency of the generated RF electric signal to reduce, or minimize, the reflected power or increase, or maximize, the return loss detected by RF interface board 104, which may improve coupling of RF energy to animal tissue. In other words, frequency may be adjusted to match the electrical load detected. The high-power tracking mode may be used in conjunction with providing the high-power output RF electric signal to increase, or maximize, the coupling of alternating RF electric field energy to animal tissue at the beginning of processing and throughout processing (e.g., impedance may change as animal tissue is processed).

Various frequencies may be used to drive RF applicator 106 for delivering energy to animal tissue. In some embodiments, the RF interface board 104 may be configured to provide an RF electric signal corresponding to frequencies in one or more industrial, scientific, or medical (ISM) frequency bands, which may be reserved in one or more countries for the use of RF energy intended for scientific, medical, and industrial uses rather than for communications. In one or more embodiments, the RF electric signal includes at least one frequency in the ISM frequency band from 2400 to 2500 MHz and may be centered, or have a peak, at 2450 MHz.

RF applicator 106 may be coupled to a receptacle that defines a processing position for animal tissue. The receptacle is configured to guide animal tissue to the processing position proximate to RF applicator 106, in which the alternating RF electric field will couple to the animal tissue. In some embodiments, such as for poultry claw processing systems, the receptacle may be described as a claw guide.

Figure 2A:
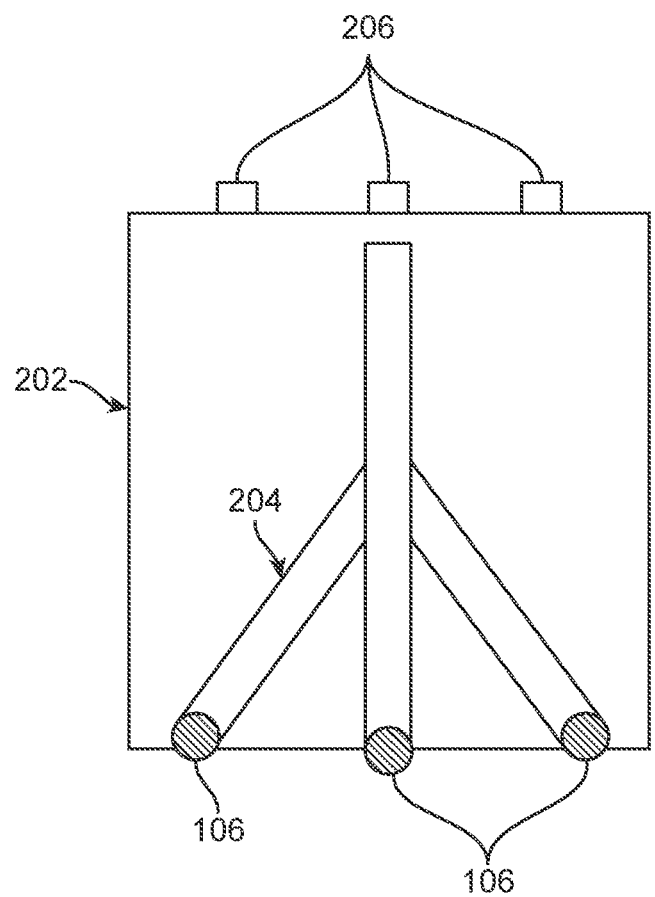
FIG. 2A illustrates RF applicators coupled to a receptacle for use in the energy delivery system of FIG. 1.

FIG. 2A shows a first side view of one example of RF applicators 106 coupled to receptacle 202. As illustrated, three RF applicators 106 are coupled to receptacle 202. Each RF applicator 106 may include one input connection 206 configured to couple to the output connection of RF interface board 104. Each RF applicator 106 may be driven independently, for example, by a different RF interface board 104. In some embodiments, input connections 206 may include coaxial connectors.

Receptacle 202 may include one or more channels 204 configured to guide animal tissue into proximity to RF applicators 106. In the illustrated embodiment, channels 204 complement the shape and size of a poultry foot and position the distal end of each poultry claw proximate to one RF applicator 106. For processing chickens, for example, channels 204 may have a shape that includes three front-claw channels extending from a rear-claw channel. Each poultry claw may be processed independently, at different times or concurrently.

Figure 2B:
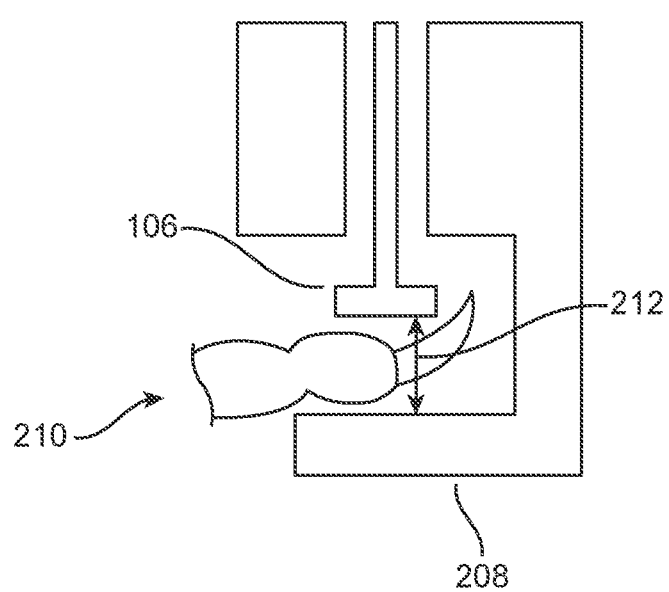
FIG. 2B illustrates one RF applicator of FIG. 2A positioned adjacent to animal tissue.

FIG. 2B shows one example of RF applicator 106 positioned adjacent to animal tissue 210. In some embodiments, at least 50, 60, 70, 80, 90, 95, 97, or even 99 percent of the RF electric field energy (of total radiated power) is directed to a volume within 10, 5, 3, 2, 1, or 0.5 centimeters from the surface of the structure. In one or more embodiments, at least 90% or at least 97% of total radiated power is directed within 10× of distance 212 from RF applicator 106 to ground plane 208 based on a finite element model, such as COMSOL for electromagnetic field modeling, of RF applicator 106. For example, a SolidWorks CAD model of the product may be provided to the finite element model along with dielectric properties, such as relative permittivity and loss factor (or loss tangent), and the total radiated power pattern may be calculated. In some embodiments, distance 212 between RF applicator 106 and ground plane 208 is about 1 mm (about 0.040 inches).

Figure 3:
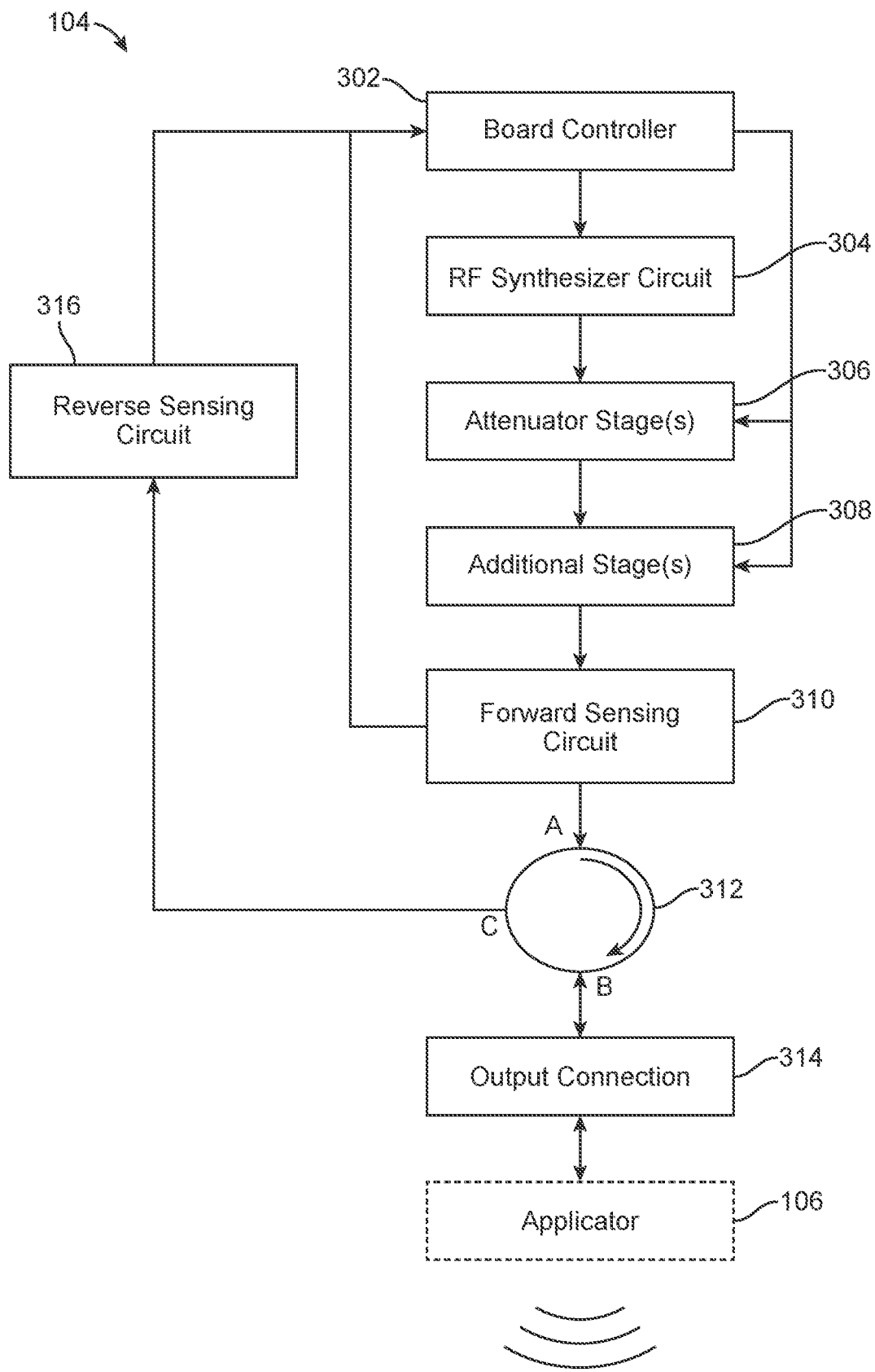
FIG. 3 illustrates one layout for the RF interface board in the energy delivery system of FIG. 1.

FIG. 3 shows one example of a layout for RF interface board 104 according to one embodiment of the present disclosure. RF interface board 104 may include one or more of: board controller 302, RF synthesizer circuit 304, one or more attenuator stages 306, one or more additional stages 308, forward sensing circuit 310, circulator 312, output connection 314, and reverse sensing circuit 316. Each component of RF interface board 104 may be coupled to, or disposed on, a single substrate. The substrate may be a printed circuit board.

Board controller 302 may be operably connected to system controller 102 to receive commands or settings. Board controller 302 may also provide data to system controller 102, such as a return loss value. In some embodiments, board controller 302 includes a communications interface, or connection, coupled wirelessly or by wire to system controller 102. In some embodiments, board controller 302 is operably connected to system controller 102 over a controller area network (CAN) bus.

Board controller 302 may be operably connected to RF synthesizer circuit 304 to provide an RF generation signal, one or more attenuator stages 306 to provide gain settings, one or more additional stages 308 to provide gain settings, forward sensing circuit 310 to detect a forward power value, and reverse sensing circuit 316 to detect a reflected power value.

As used herein, the term "gain setting" refers to a gain value or gain parameter and may correspond to gains that attenuate (e.g., negative dB) or amplify (e.g., positive dB). For example, a higher magnitude gain setting may further attenuate or amplify a signal depending on whether the gain setting is positive or negative.

RF synthesizer circuit 304 is configured to generate an RF electric signal in response to the RF generation signal. RF synthesizer circuit 304 may be configured to generate RF electric signal at one or more frequencies. For example, RF synthesizer circuit 304 may generate an RF electric signal containing frequencies in one or more ISM frequency bands.

One or more attenuator stages 306 may be operably connected to an output of RF synthesizer circuit 304. At least one attenuator stage 306 is configured to provide an intermediate RF electric signal based on the generated RF electric signal. Each attenuator stage 306 includes an attenuator and optionally an amplifier. The generated RF electric signal may be attenuated or amplified by one or more attenuator stages 306 to provide the intermediate RF electric signal. Each attenuator stage 306 may be described as a preamplification stage.

One or more additional stages 308 may be operably connected to an output of attenuator stages 306. Additional stages 308 are configured to provide an output RF electric signal based on the intermediate RF electric signal. In some embodiments, the intermediate RF electric signal is amplified by one or more additional stages 308 to provide the output RF electric signal. Additional stages 308 may be more specifically described as driving stages or amplification stages.

Forward sensing circuit 310 may be operably connected to an output of additional stages 308. Forward sensing circuit 310 is configured to provide a forward power value based on a measurement of the output RF electric signal. Forward sensing circuit 310 may include a power detector, which may be electromagnetically isolated, or shielded, from other parts of RF interface board 104. Forward sensing circuit 310 may include an output to provide the forward power value to board controller 302 and may include a through port to provide the output RF electric signal.

Circulator 312 may be operably connected to the through port of forward sensing circuit 310 to receive the output RF electric signal. Circulator 312 may include multiple ports A, B, C that continuously provide a signal received at each port to a subsequent port in a circular manner. Each port is configured to concurrently receive and provide different signals. For example, a signal received at port A is provided to port B, a signal received at port B is provided to port C, and a signal received at port C is provided to port A.

In the illustrated embodiment, port A of circulator 312 is operably connected to the through port of forward sensing circuit 310 to receive the output RF electric signal. Circulator 312 provides the output RF electric signal to port B. RF applicator 106 may be operably connected to port B of circulator 312 to receive the output RF electric signal. RF applicator 106 may provide an alternating RF electric field in response to the output RF electric signal. Some energy or power of output RF electric signal may be reflected by RF applicator 106 back to port B of circulator 312. Any portion of output RF electric signal reflected by RF applicator 106 to port B may be provided by circulator 312 to port C.

Reverse sensing circuit may be operably connected to port C of circulator 312. Reverse sensing circuit 316 is configured to provide a reflected power value based on a measurement of the reflected portion of the output RF electric signal. Reverse sensing circuit 316 may include a power detector, which may be electromagnetically isolated, or shielded, from other parts of RF interface board 104. Reverse sensing circuit 316 may include an output to provide the reflected power value to board controller 302 and may include a through port, for example, to provide energy from the reflected RF electric signal to electrical ground through an impedance element.

RF applicator 106 may be configured to be sensitive to the presence of animal tissue in proximity to RF applicator 106. In some embodiments, RF interface board 104 may be calibrated to not match impedance with air but, rather, match impedance with animal tissue positioned proximate, or adjacent, to RF applicator 106 in the processing position. Impedance matching RF interface board 104 with animal tissue may increase, or provide a maximum amount of, energy delivered to animal tissue. In other words, the reflected portion of output RF electric signal is greater when no animal tissue is in the processing position compared to when animal tissue is in the processing position.

As used herein, the term "impedance match" refers to designing an input impedance of an electrical load (e.g., animal tissue) or the output impedance of a corresponding signal source (e.g., RF interface board) to substantially maximize or optimize the power transfer or minimize signal reflection from the electrical load. For example, in some embodiments, the system including the RF interface board may change RF electric signal frequency in order to impedance match the output impedance of the RF interface board with the input impedance of the animal tissue, which may substantially maximize power transfer to the animal tissue, within the constraints of the RF interface board and the system.

Board controller 302 may receive both the forward and reflected power values. Board controller 302 may be configured to determine a return loss based on the forward and reflected power values (e.g., forward power value minus reflected power value). The return loss may be greater when animal tissue is in the processing position compared to when animal tissue is not in the processing position.

The return loss may be communicated to system controller 102. Based on the return loss, system controller 102 may issue different commands to board controller 302. For example, when return loss rises above a return loss threshold value (or reflected power drops or falls below a reflected power threshold value), system controller 102 may issue one or more commands to board controller 302 to provide a high-power RF output electric signal and to enter the high-power tracking mode. In some embodiments, board controller 302 may also be configured to enter into a non-high-power tracking mode, such as a low-power tracking mode.

The return loss threshold value may be determined based on a baseline return loss value. For example, the loss threshold value may be at least 1, 2, 3, 4, or 5 dBm greater than the baseline return loss.

One or more of the components, such as controllers, synthesizers, interfaces, sensors (e.g., power or temperature), amplifiers, and attenuators, described herein may include a processor, such as a central processing unit (CPU) or microcontroller unit (MCU), computer, logic array, or other device capable of directing data coming into or out of the RF interface board of energy delivery system. The controller may include one or more computing devices having memory, processing, and communication hardware. The controller may include circuitry used to couple various components of the controller together or with other components operably coupled to the controller. The functions of the controller may be performed by hardware and/or as computer instructions on a non-transient computer readable storage medium.

The processor of the controller may include any one or more of a microprocessor, a microcontroller, a digital signal processor (DSP), an application specific integrated circuit (ASIC), a field-programmable gate array (FPGA), and/or equivalent discrete or integrated logic circuitry. In some examples, the processor may include multiple components, such as any combination of one or more microprocessors, one or more controllers, one or more DSPs, one or more ASICs, and/or one or more FPGAs, as well as other discrete or integrated logic circuitry. The functions attributed to the controller or processor herein may be embodied as software, firmware, hardware, or any combination thereof. While described herein as a processor-based system, an alternative controller could utilize other components such as relays and timers to achieve the desired results, either alone or in combination with a microprocessor-based system.

In one or more embodiments, the exemplary systems, methods, and interfaces may be implemented using one or more computer programs using a computing apparatus, which may include one or more processors and/or memory. Program code and/or logic described herein may be applied to input data/information to perform functionality described herein and generate desired output data/information. The output data/information may be applied as an input to one or more other devices and/or methods as described herein or as would be applied in a known fashion. In view of the above, it will be readily apparent that the controller functionality as described herein may be implemented in any manner known to one skilled in the art.

Figure 4:
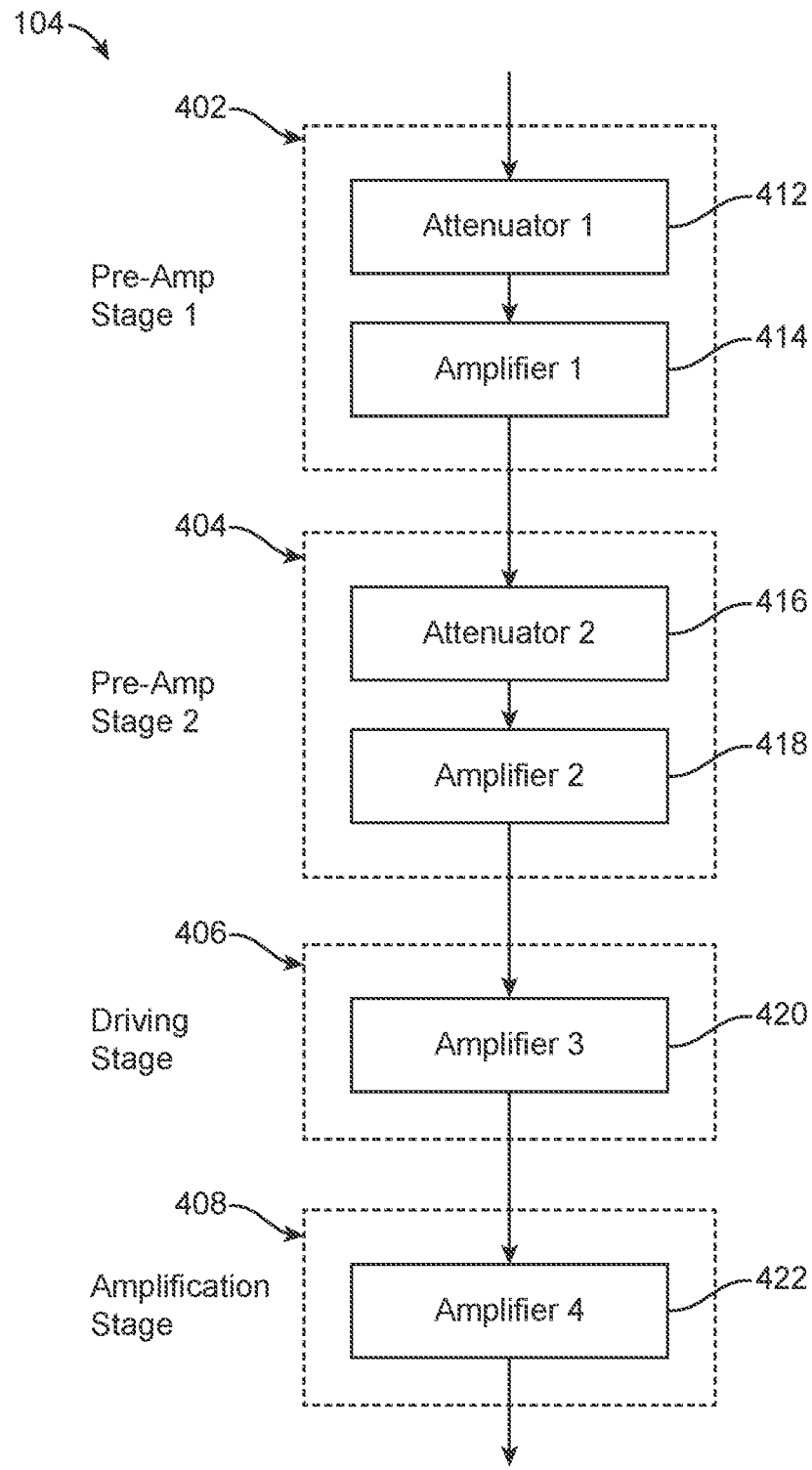
FIG. 4 illustrates one layout for various stages of the RF interface board in the energy delivery system of FIG. 1.

FIG. 4 shows one example of a layout for various stages of RF interface board 104, which may include one or more of: first preamplification stage 402, second preamplification stage 404, driving stage 406, and amplification stage 408. Each stage may correspond to a circuit including an attenuator, an amplifier, or both. RF interface board 104 may include one or more of: first attenuator 412, first amplifier 414, second attenuator 416, second amplifier 418, third amplifier 420, and fourth amplifier 422. Each attenuator may be described as a variable voltage attenuator (VVA).

First preamplification stage 402 may be operably connected to an output of RF synthesizer circuit 304 to receive generated RF electric signal. First preamplification stage 402 may dynamically attenuate or amplify the generated RF electric signal. In some embodiments, first preamplification stage 402 may include first attenuator 412 and first amplifier 414. First amplifier 414 may be operably connected to an output of first attenuator 412. First amplifier 414 may amplify a signal attenuated by first attenuator 412.

In some embodiments, first attenuator 412 may be operably connected to board controller 302 and may be modulated, or adjusted, with a gain setting to dynamically attenuate the generated RF electric signal. First attenuator 412 may be configured to attenuate from a low attenuation value to a high attenuation value. In some embodiments, board controller 302 may be configured to not adjust the gain setting of first amplifier 414 to dynamically attenuate or amplify the generated RF electric signal. First amplifier 414 may be configured to amplify at a fixed amplification value.

To provide the dynamic gain range of first preamplification stage 402, the attenuation values of first attenuator 412 may encompass the fixed amplification value of first amplifier 414. For example, the dynamic gain range of first attenuator 412 may be from a low attenuation value of −4 dB to a high attenuation value of −32 dB, and the fixed amplification value of first amplifier 414 may be 15 dB. By adjusting the gain setting of first attenuator 412 from the low attenuation value to the high attenuation value, the dynamic gain range of the first preamplification stage 402 may extend from 11 dB to −17 dB.

Second preamplification stage 404 may be operably connected to an output of first preamplification stage 402. Second preamplification stage 404 may have the same or similar aspects of first preamplification stage 402. Like first preamplification stage 402, second preamplification stage 404 may dynamically attenuate or amplify the generated RF electric signal. In some embodiments, second preamplification stage 404 may include second attenuator 416 and first amplifier 414. Second amplifier 418 may be operably connected to an output of second attenuator 416.

Also, in some embodiments, second attenuator 416 may be operably connected to board controller 302 and may be adjusted with a gain setting to dynamically attenuate or amplify the generated RF electric signal. Second attenuator 416 may be configured to attenuation from a low attenuation value to a high attenuation value. The high and low attenuation values may be the same or different than the attenuation values of first attenuator 412. In other words, the attenuation range of second attenuator 416 may be the same or different than the attenuation range of first attenuator 412. In some embodiments, board controller 302 may be configured to not adjust the gain setting of second amplifier 418 to dynamically attenuate or amplify the generated RF electric signal. Second amplifier 418 may be configured to amplify at a fixed amplification value, which may be the same or different as the fixed amplification value of first amplifier 414.

To provide the dynamic gain range of first second preamplification stage 404, the attenuation values of second attenuator 416 may encompass the fixed amplification value of second amplifier 418. Like first preamplification stage 402, in some embodiments, by adjusting the gain setting of second attenuator 416 from the low attenuation value to the high attenuation value, the dynamic gain range of the second preamplification stage 404 may extend from 11 dB to −17 dB.

Using the example gain ranges described above, the preamplification stages 402, 404 together may provide a dynamic gain range from 22 dB to −34 dB. In other words, an intermediate RF electric signal provided by the preamplification stages 402, 404 together may correspond to a generated RF electric signal dynamically attenuated 34 dB (e.g., a gain of −34 dB) or amplified 22 dB.

The gain setting for second attenuator 416 may be the same or different than the gain setting for first attenuator 412. In some embodiments, board controller 302 increases the attenuation value of second attenuator 416 before increasing the attenuation value of first attenuator 412, which may improve the noise floor throughout the dynamic gain range of the combined preamplification stages 402, 404.

In some embodiments, only the gain settings of one or more attenuators may be adjusted. In other words, the gain settings of one or more amplifiers may not be adjusted to change the power level of the output RF electric signal. In general, adjusting the gain values of attenuators instead of amplifiers may improve the control of RF interface board 104 to provide a precise power level of the output RF electric signal.

Driving stage 406 may include third amplifier 420 operably connected to an output of second preamplification stage 404 to receive the intermediate RF electric signal. Third amplifier 420 may have a fixed amplification value. For example, the fixed amplification value of third amplifier 420 may be 20 dB. The dynamic gain range of the preamplification stages 402, 404 in combination with driving stage 406 may be 42 dB to −14 dB. In some embodiments, third amplifier 420 may have a 10 W (+40 dBm) maximum output power.

Amplification stage 408 may include fourth amplifier 422 operably connected to an output of driving stage 406 and configured to provide the output RF electric signal in response to receiving the intermediate RF electric signal. Fourth amplifier 422 may have a fixed amplification value. For example, the fixed amplification value of fourth amplifier 422 may be 20 dB. The dynamic gain range of the preamplification stages 402, 404 in combination with driving stage 406 and amplification stage 408 may be 62 dB to 6 dB. In some embodiments, fourth amplifier 422 may have a 140 W (+51.5 dBm) maximum output power.

In addition to providing a wide dynamic gain range, RF interface board 104 may be configured to provide high resolution throughout the range. A digital-to-analog converter (DAC), which may be included in, or coupled to, board controller 302, may be used to provide gain settings to one or more attenuators or amplifiers. In some embodiments, a DAC providing gain settings to first and second attenuators 412, 416 may be used to provide an output RF electric signal with a step size less than or equal to dB over an entire target output power range. The step size may be equal to about 0.05 dB. In some embodiments, a 12-bit DAC may be used.

The target output power range may be selected based on the particular application. The target output power range may range from, for example, 1 mW to 125 W, or about five orders of magnitude. The target dB range, or power ratio between the high- and low-power output RF electric signals, may be at least 5, 10, 15, 20, 30, 40, 50, or 60 dB. One example of a target output power range is from 17 to 47 dBm. In some examples, the target output power range may have a low end of 0 dBm.

Contrary to other types of designs, the output RF electric signal may be substantially immune to changes in impedance load. For example, whether or not animal tissue is in the processing position, the output RF electric signal may not change (measurable using the forward power value). In some embodiments, the output RF electric signal changes less than +/−0.25 dB whether or not animal tissue is in the processing position. The presence of animal tissue may represent an impedance match (e.g., about 50 ohms for a poultry claw) and the absence of animal tissue may represent a mismatch (e.g., open circuit). With the output RF electric signal being substantially immune to changes in impedance load, RF interface board 104 may not need to substantially change gain settings when animal tissue is placed in or removed from the processing position. However, in some embodiments, the board controller 302 may use the measured forward power value to maintain a constant power for output RF electric signal, for example, but adjusting gain settings.

Figure 5:
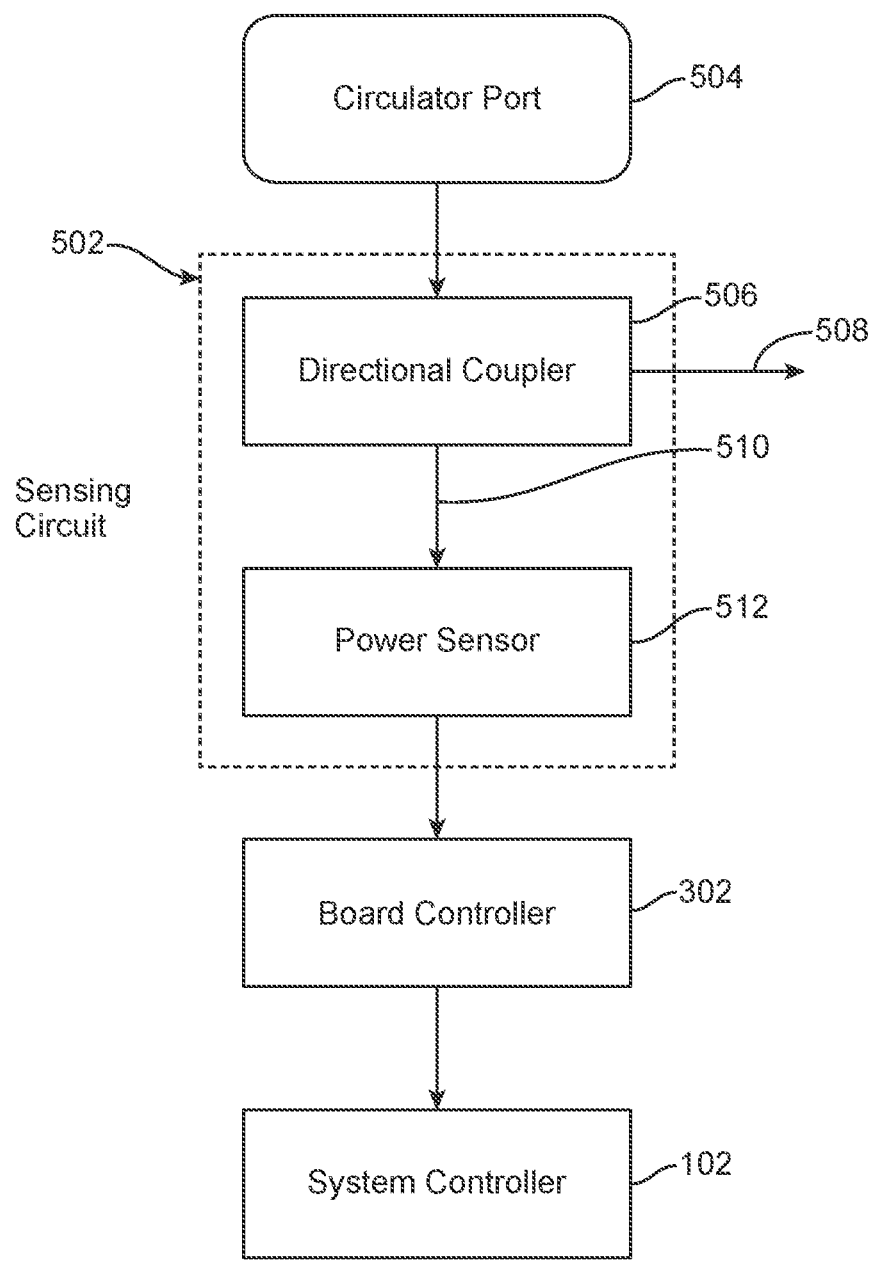
FIG. 5 illustrates one layout for a sensing circuit used in the RF interface board of FIG. 3.

FIG. 5 shows one example of a layout for sensing circuit 502. Sensing circuit 502 may be operably coupled to circulator port 504. Sensing circuit may include directional coupler 506 and power sensor 512. Directional coupler 506 is configured to receive a power signal from circulator port 504. Directional coupler 506 is configured to provide a sensing signal to coupling port 510, which is isolated from the transmitted signal provided to through port 508. Most of the energy from the power signal may be contained in the transmitted signal provided to through port 508. The sensing signal may contain only a fraction of the power signal. In some embodiments, the sensing signal corresponds to −30, −40, or −50 dB of the power signal. In some embodiments, the ratio of power at through port 508 to power at coupling port 510 is 1000 to 1, or about −30 dB. Directional coupler 506 may also be described as a power divider. In general, the directional coupler 506 may desirably have tightly controlled coupling, low insertion loss, and an operation frequency range from 1400 to 2700 MHz.

Power sensor 512 may be operably connected to coupling port 510 of directional coupler 506 to provide a power value based on the reduced-power sensing signal representing the power signal from circulator port 504. Sensing circuit 502 may also include other components (not shown), such as an analog-to-digital converter (ADC) and a temperature sensor. Power sensor 512 may be coupled to an analog-to-digital converter (ADC), which may be considered part of sensing circuit 502 or board controller 302. In some embodiments, board controller 302 may be described as a board control circuit, which may include one or more processors or microcontrollers.

Board controller 302 may be operably connected to power sensor 512 to receive the power value, which may represent a forward or reflected power value. Board controller 302 may be configured to provide a return loss value based on the forward and reflected power values. Board controller 302 may report the return loss value to system controller 102.

Figure 6:
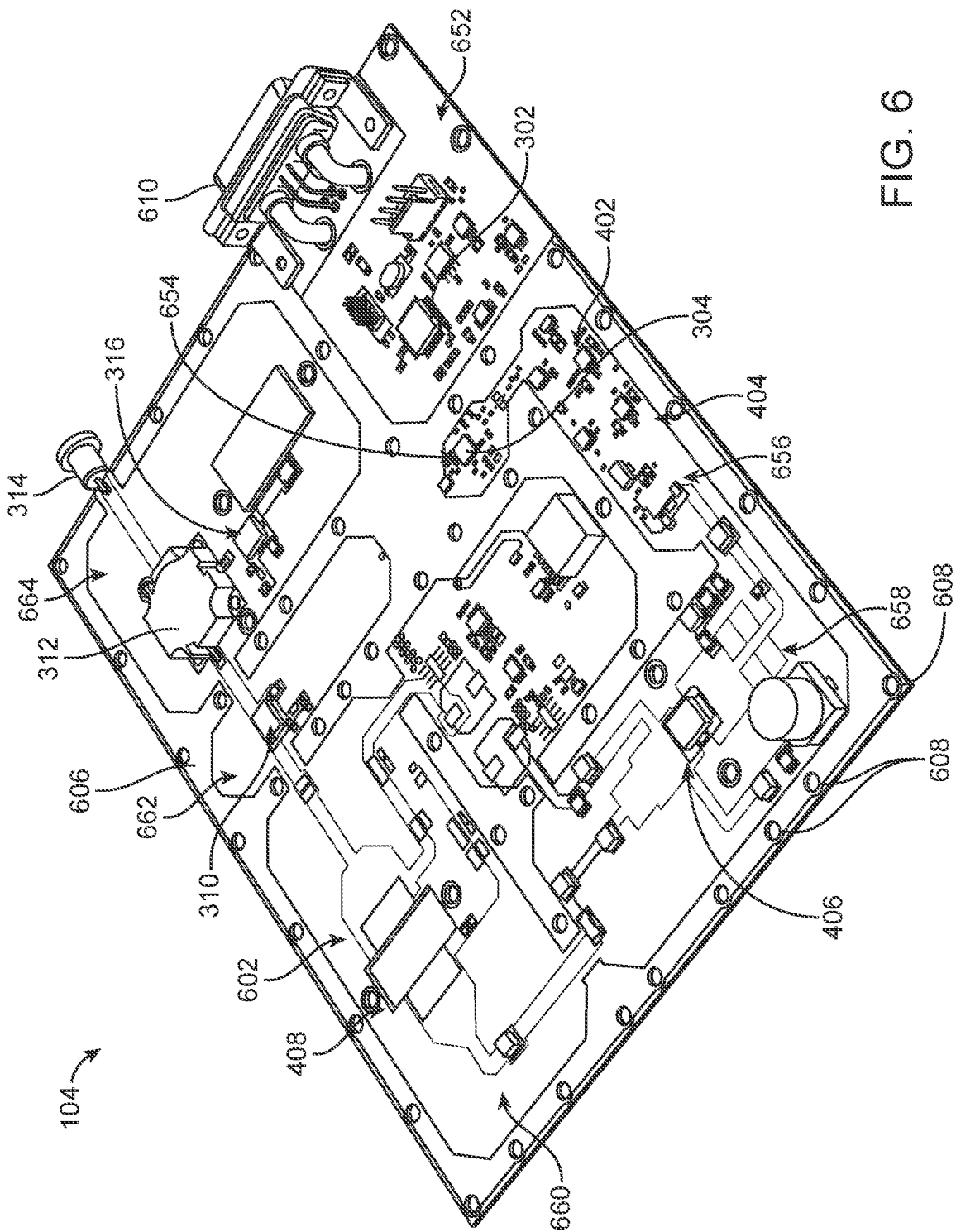
FIGS. 6 and 7 illustrate a front major surface and a second major surface, respectively, of one physical layout of the RF interface board of FIG. 3.
Figure 7:
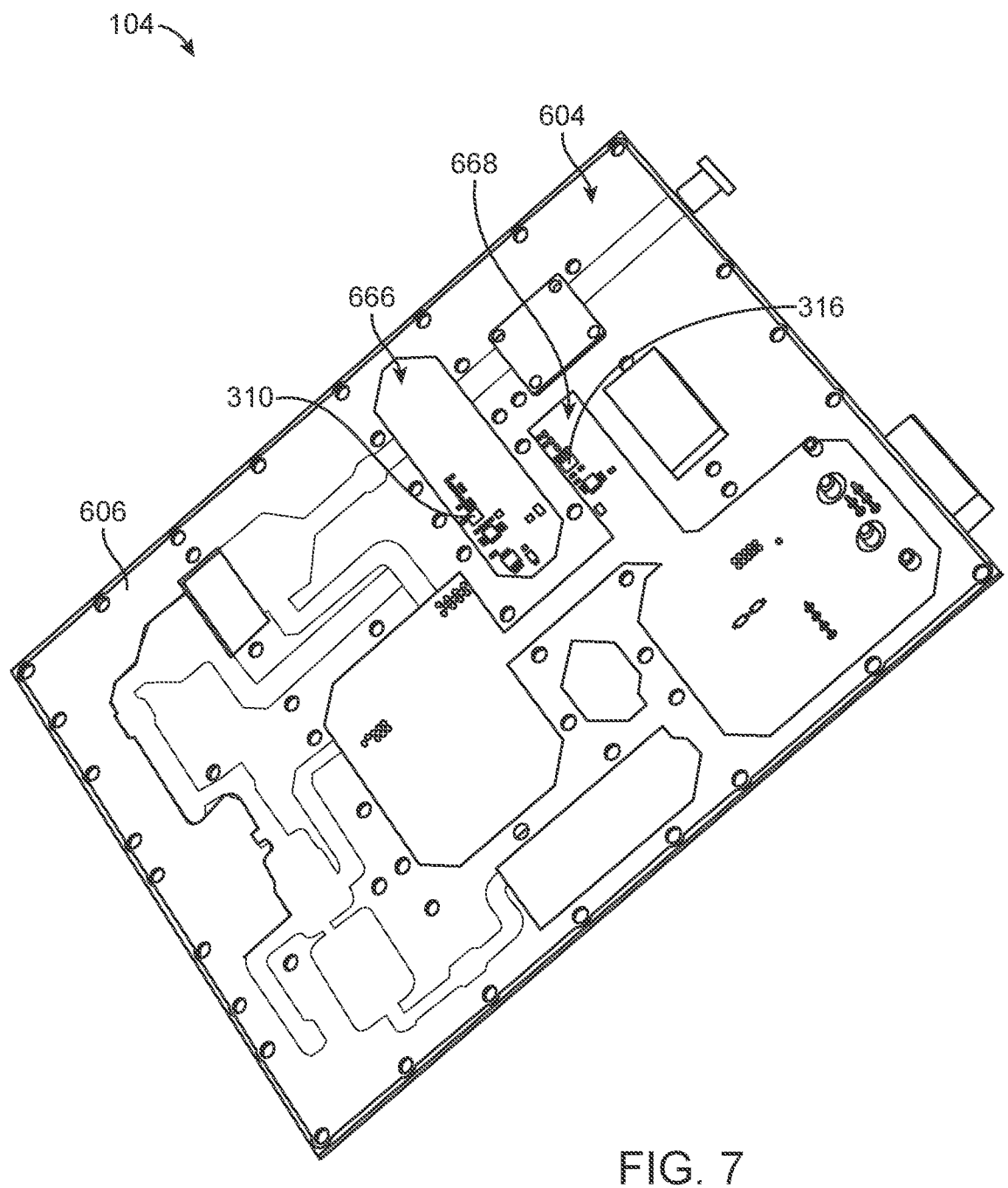

FIGS. 6 and 7 show one example of a physical layout for RF interface board 104. As shown, RF interface board 104 is a printed circuit board, which may have multiple layers. FIG. 6 shows first major surface 602, or top surface, of RF interface board 104, and FIG. 7 shows second major surface 604, or bottom surface, in a mirror view. Second major surface 604 is on an opposite side of RF interface board 104 from first major surface 602. As used herein, the term "major surface" refers to a surface that is substantially parallel to each layer of the printed circuit board.

RF interface board 104 includes one or more regions. Each region may be partially or fully electromagnetically shielded, or isolated, from other regions using a housing. RF interface board 104 may include a ground trace 606, or ground conductor, that extends between one or more regions to facilitate shielding. Ground trace 606 may be positioned on first major surface 602 and second major surface 604. One or more apertures 608 may extend through ground trace 606, which may be used to fasten an electromagnetic shielding structure to RF interface board 104. The electromagnetic shielding structure may be used to create a compartment around each region to facilitate noise isolation of various components and may extend around the perimeter of RF interface board 104 to facilitate emissions control.

RF interface board 104 may include one or more of: first region 652, second region 654, third region 656, fourth region 658, fifth region 660, sixth region 662, seventh region 664, eighth region 666, and ninth region 668. In the illustrated embodiment, all of the regions are positioned on the first major surface 602 except for eighth and ninth regions 666, 668, which are positioned on second major surface 604.

On first major surface 602, first region 652 may include board controller 302. Second region 654 may include RF synthesizer circuit 304. Third region 656 may include one or more preamplification stages 402, 404. Fourth region 658 may include driving stage 406. Fifth region 660 may include amplification stage 408. Sixth region 662 may include part of forward sensing circuit 310. Seventh region 664 may include circulator 312 and part of reverse sensing circuit 316.

On second major surface 604, eighth region 666 may include part of forward sensing circuit 310, such as power sensor 512 (FIG. 7). Eighth region 666 may be positioned opposite to sixth region 662. Ninth region 668 may include part of reverse sensing circuit 316, such as power sensor 512 (different than power sensor 512 of forward sensing circuit 310). Ninth region 668 may be positioned opposite to seventh region 664.

Communication connection 610 may be operably connected to first region 652, and output connection 314 may be operably connected to seventh region 664.

The forward and reverse sensing circuits 310, 316 may be accurate over the entire target output power range. In some embodiments, measurements of forward and reflected power values may be accurate within +/−0.25 dB over an output power range from 17 to 47 dBm. Reflected power values may be accurate within +/−0.25 dB over an even larger range, such as from 3 to 47 dBm, compared to forward power values. The accuracy of forward and reverse sensing circuits 310, 316 may be maintained over one or more ISM frequency bands, such as the 2400 to 2500 MHz ISM frequency band. The frequency of RF electric signal may be centered, or have a peak, at 2450 MHz. In other embodiments, the frequency of RF electric signal may be centered, or have a peak, at 915 MHz within the 902 to 928 MHz ISM frequency band.

Further, the forward and reverse sensing circuits 310, 316 may be accurate within a target operating temperature range. In some embodiments, forward and reflected power values may accurate within +/−0.3 dB over a temperature range of 20 to 40° C. Using temperature sensors, the forward and reflected power values may be compensated to be accurate within +/−0.1 dB.

Figure 8:
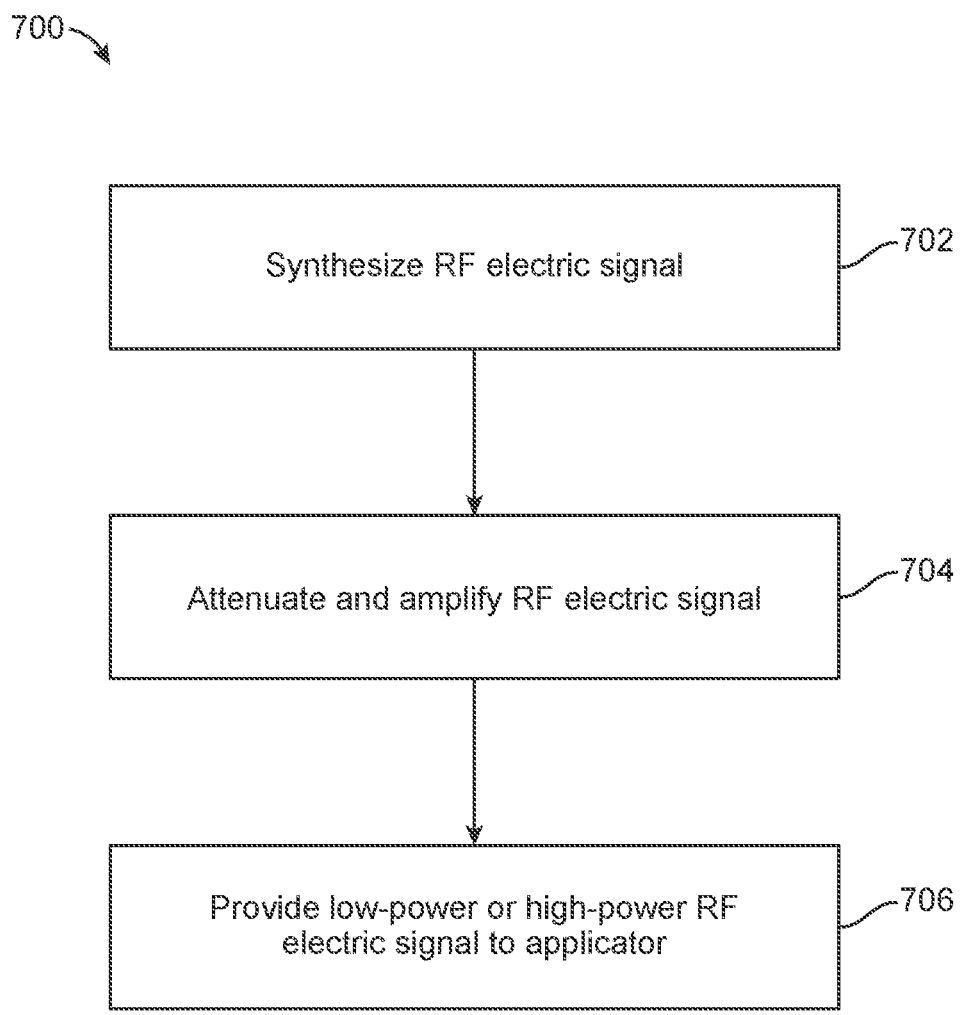
FIG. 8 illustrates one method for using the RF interface board of FIG. 3.

FIG. 8 shows one method 700 for using RF interface board 104 in energy delivery system 100. Method 700 may include synthesizing an RF electric signal 702, which may also be described as a generated RF electric signal. The RF electric signal may have frequency content in one or more ISM frequency bands.

Method 700 may continue to attenuate and amplify the RF electric signal 704. Some amplifiers may not provide accurate and precise gain control at low gains. Attenuators may be used to provide a dynamic gain range, particularly in the preamplification stage.

Method 700 may continue to provide a low-power or high-power electric signal to an RF applicator 706. The low-power RF output electric signal may be used to generate a low-power alternating RF electric field using the RF applicator. The low-power field may be used for sensing the presence of animal tissue near the RF applicator. The high-power RF output electric signal may be used to generate a high-power alternating RF electric field using the RF applicator. The low-power field may be used for sensing animal tissue near the RF applicator.

Figure 9:
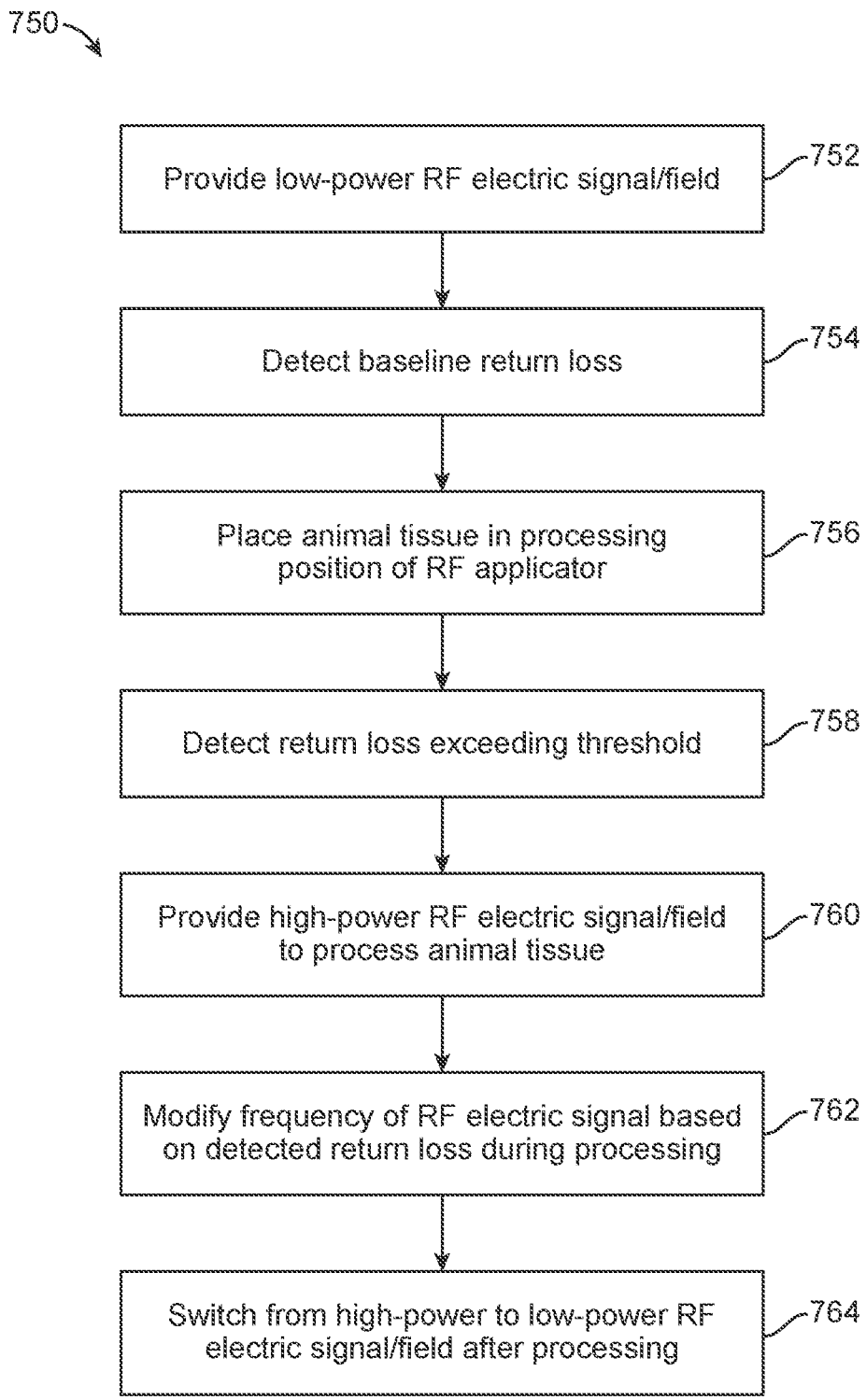
FIG. 9 illustrates one specific method for carrying out the method of FIG. 8.

FIG. 9 shows method 750, which is one example for carrying out method 750 of FIG. 8. Method 750 may include providing a low-power RF output electric signal to an RF applicator, such as RF applicator 106, which may generate a low-power RF electric field 752. Method 750 may continue and detect a return loss from the RF applicator 754, which may be a baseline return loss corresponding to no animal tissue in the processing position of the RF applicator.

Animal tissue to be processed may be placed in the processing position of the RF applicator 756. In some embodiments, the RF applicator may be moved to the animal tissue. In some embodiments, machine vision may be used to position animal tissue near the RF applicator.

The return loss detected after positioning the animal tissue may exceed a threshold value 758. For example, the RF interface board may measure the return loss and communicate the return loss to the system controller. The return loss may be compared to a threshold value stored or determined by the system controller. When more than one RF applicator is used, for example, to detect more than one poultry claw, the average return loss associated with each RF applicator may be compared to the threshold value.

In some embodiments, the threshold value may be greater than or equal to 1, 2, 3, 4, 5, or 6 dB. When the measured return loss exceeds the threshold value, the system controller may issue a command to RF interface board to provide a high-power output RF electric signal, which may generate a high-power RF electric field to couple to the animal tissue 760. The animal tissue may be processed in response to received energy from the high-power RF electric field.

When more than one RF applicator is used, each RF applicator may process tissue concurrently or sequentially. In other words, the high-power RF electric field may be provided to each RF applicator concurrently or at different times.

The system controller may issue a command to RF interface board to modify the frequency of the RF electric signal based on the detected return loss during processing 762. The frequency content may be contained in one or more ISM frequency bands, even after being adjusted. In some embodiments, the board controller may sweep the frequency within one or more ISM frequency bands. For example, the frequency of the RF electric signal may be swept using the RF synthesizer circuit in the 2400 to 2500 MHz ISM frequency band in increments of 1 MHz or less (e.g., for finer control). The frequency resulting in the lowest return loss may be selected and used during delivery of the high-power RF electric field to the animal tissue. The frequency may be modified one or more times during delivery of the high-power RF electric field.

Method 750 may continue to switch into a monitoring mode, in which the high-power RF electric signal is switched to a low-power RF electric signal, to generate a low-power RF electric field 764, once again, particularly when processing of the animal tissue has been completed. The RF interface board may be switched into a monitoring mode. In some embodiments, processing of the animal tissue may be completed after a predetermined duration or time period has elapsed. For example, the high-power RF electric signal may range from 10 to 30 W (e.g., about 40 to 45 dBm) and be delivered for about 1 second to process a poultry claw. In some embodiments, about 1 J of energy is delivered to each poultry claw.

The high-power output RF electric signal may be selected based on the particular application. In some embodiments, the high-power output RF electric signal may have power in a range from 10 to 50 W.

In some embodiments, detecting a baseline return loss 754 and detecting the return loss exceeding the threshold value 758 may include correcting the return loss value for compensate for drift. For example, the power sensor may drift due to changes in temperature or frequency.

Figure 10:
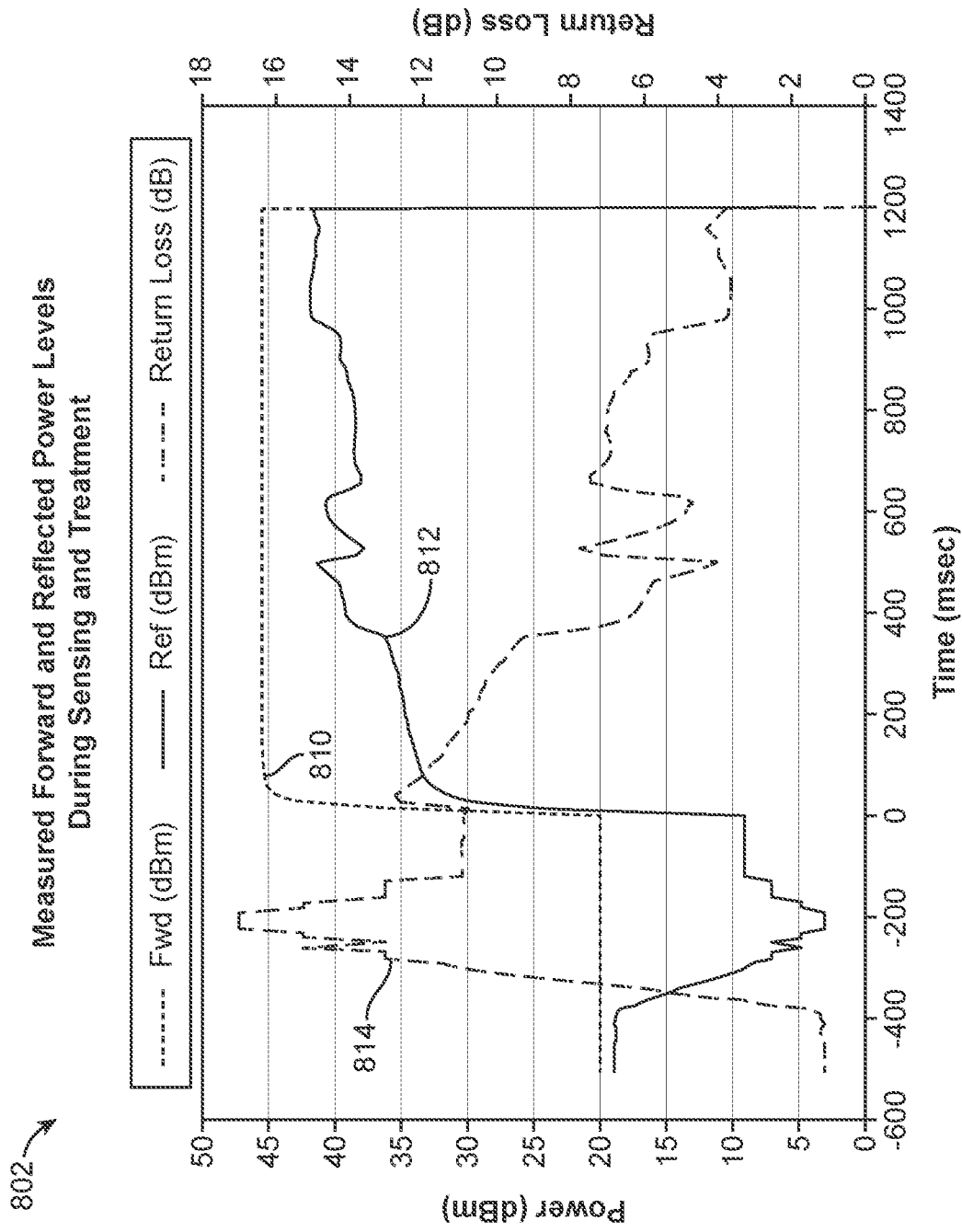
FIGS. 10 and 11 plot measurements of sensing power values versus time with and without enabling a high-power tracking mode, respectively, on the RF interface board of FIG. 3.
Figure 11:
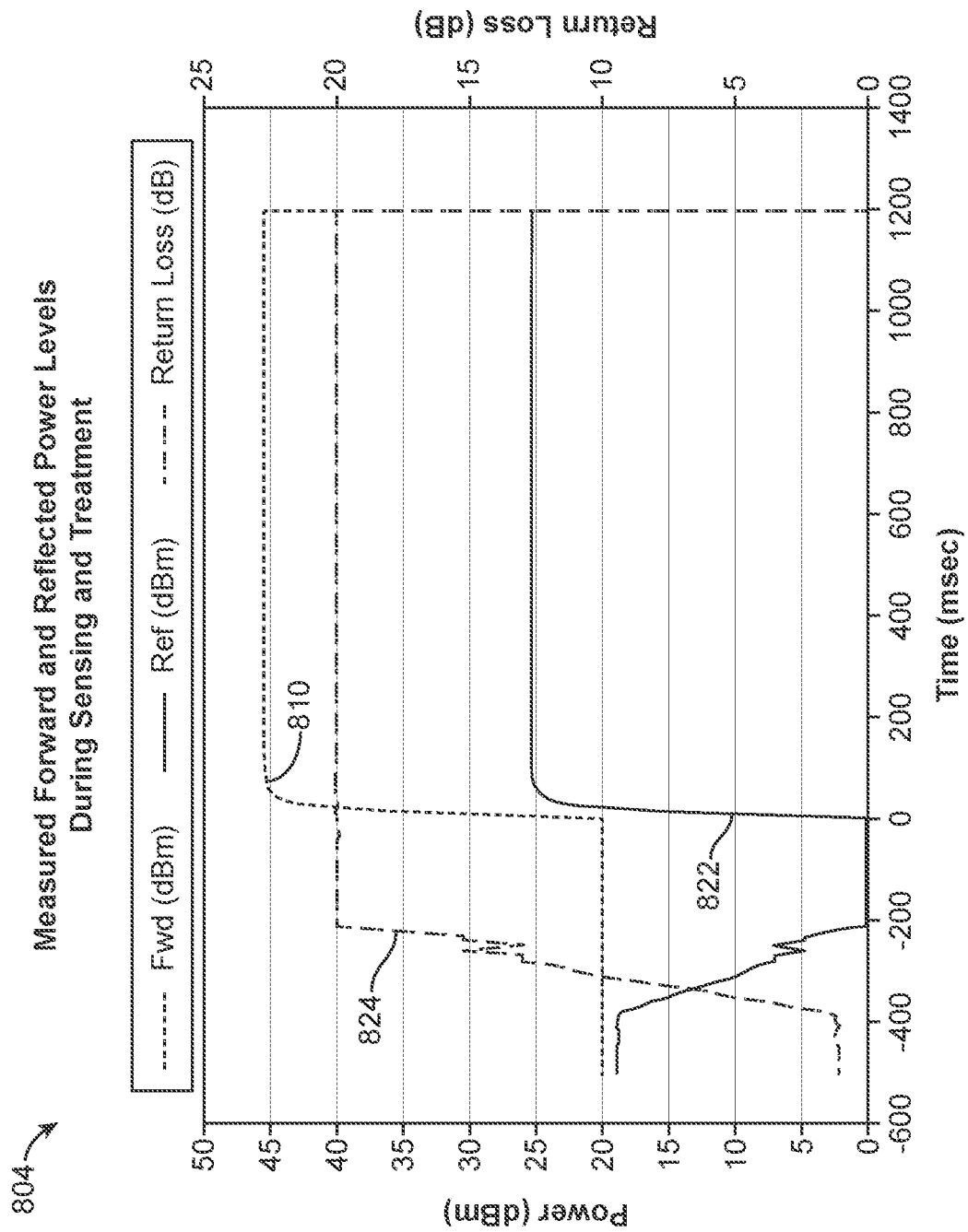

FIGS. 10 and 11 show plots of measured sensing power values (dBm) versus time (milliseconds) with and without high-power tracking mode, in which frequency is adjusted to match the load, using system 100 of FIG. 1 for one example of animal tissue. Plot 802 of FIG. 10 shows reflected power values 812 and calculated return losses 814 in response to forward power values 810 without the use of high-power tracking mode on the RF interface board. Plot 804 of FIG. 11 shows reflected power values 822 and calculated return losses 824 in response to forward power values 810 with high-power tracking mode turned on.

Forward power values 810 include sensing power values of 20 dBm starting at about −500 milliseconds. Reflected power values 812, 822 are high (corresponding to low return losses 814, 824) until the animal tissue is inserted into the receptacle and moved toward the processing position at about −400 milliseconds. When the animal tissue is being positioned, a rapid decrease in reflected power values 812, 822 (corresponding to increasing return losses 814, 824) is detected while the tissue is being properly positioned. Processing begins at 0 milliseconds. As illustrated, forward power values 810 climbs rapidly to the processing power of about 45.4 dBm and lasts for about 1.2 seconds.

In plot 802, when high-power tracking mode is not used, reflected power values 812 may gradually increase during the first 350 milliseconds of processing, which may be due to tissue heating and may change from animal to animal. Large jumps in reflected power values 812 may be the result of physical movements of animal tissue relative to the RF applicator. Reflected power values 812 may continue to rise for the remainder of the processing time as the tissue continues to heat. Forward power may shut off at 1200 milliseconds and forward power values 810 may drop when processing is complete.

In contrast to plot 802, plot 804 shows the resulting reflected power values 822 and return losses 824 when high-power tracking mode is used. In general, the goal of high-power tracking mode may be to maintain a constant return loss throughout processing. As illustrated, reflected power values 822 and return losses 824 may remain constant, or substantially constant, from the start of processing at 0 milliseconds through the completion of processing at 1200 milliseconds.

Figure 12:
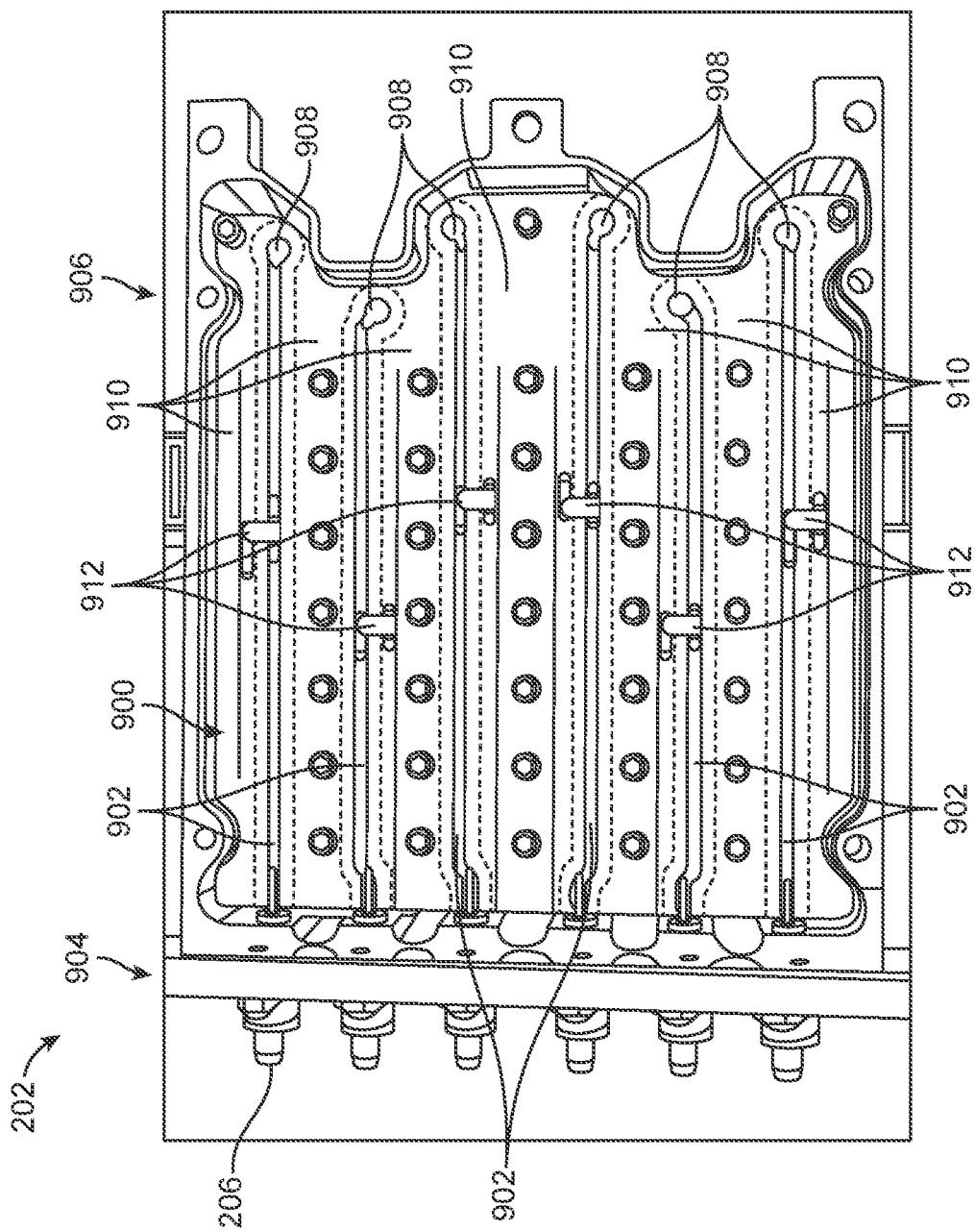
FIG. 12 illustrates one example of a second side of the receptacle different than the first side shown in FIG. 2A.

FIG. 12 shows one example of a second side of receptacle 202 different than the first side shown in FIG. 2A. In particular, the first side of receptacle 202 shown in FIG. 2A shows only half of the receptacle 202 shown in FIG. 12. For example, FIG. 2A shows only three input connections 206, or input connectors, whereas FIG. 12 shows six input connections 206 to deliver energy to all six poultry toes.

Receptacle 202 may also be described as a toe guide assembly. Receptacle 202 may include tuning board 900, which may be a printed circuit board including various conductive paths and electrical components coupled to a substrate that deliver an RF electric signal from one or more input connections 206 to one or more RF applicators 106 (FIG. 2A). The receptacle 202 may be tuned for delivering RF energy to tissue positioned proximate to each RF applicator 106 using tuning board 900.

In the illustrated embodiment, tuning board 900 is operably coupled to six input connections 206. Although tuning board 900 is shown with six input connectors 206, tuning board 900 may include any suitable number of input connections 206. Each input connections 206 is operably coupled to a different conductor 902. Each conductor 902 extends from input region 904 of receptacle 202 to applicator region 906 of receptacle 202. Each conductor 902 is operably coupled to a different applicator connection 908, which may include a solder joint through a via. In turn, each applicator connection 908 may be operably coupled to a different RF applicator 106.

Conductors 902 may extend along any suitable path from input region 904 to applicator region 906. In the illustrated embodiment, conductors 902 are generally straight and linear.

Each conductor 902 and corresponding applicator connection 908 may be separated from ground plane 910, for example, by the absence of conductive material on the printed circuit board. In general, each conductor 902 is operably coupled, for example, to a corresponding ground plane 910 to form a 50-ohm transmission line for an RF signal. Ground plane 910 may be electrically coupled to one or more grounding connection points, which are shown as conductive protrusions, or bolts, coupled to tuning board 900. The grounding connection points may electrically couple ground plane 910 to an electromagnetically shielding housing.

One or more capacitors 912 may be positioned along one or more conductors 902. In the illustrated embodiment, each capacitor 912 is electrically coupled between one conductor 902 and ground plane 910. Each capacitor 912 may be used to tune a corresponding RF applicator 106 to reach a target frequency. In particular, placement of capacitor 912 along conductor 902, for example, closer to input region 904 or closer to applicator region 906, may change the resonant frequency of the corresponding RF applicator 106.

Capacitors 912 may be described as tuning components. Although capacitors 912 are shown, any suitable tuning component may be used that is available to one skilled in the art who has the benefit of this disclosure. Non-limiting examples of other tuning components include inductors, wire, integrated circuit board capacitance, and quarter-wave matching.

Figure 13:
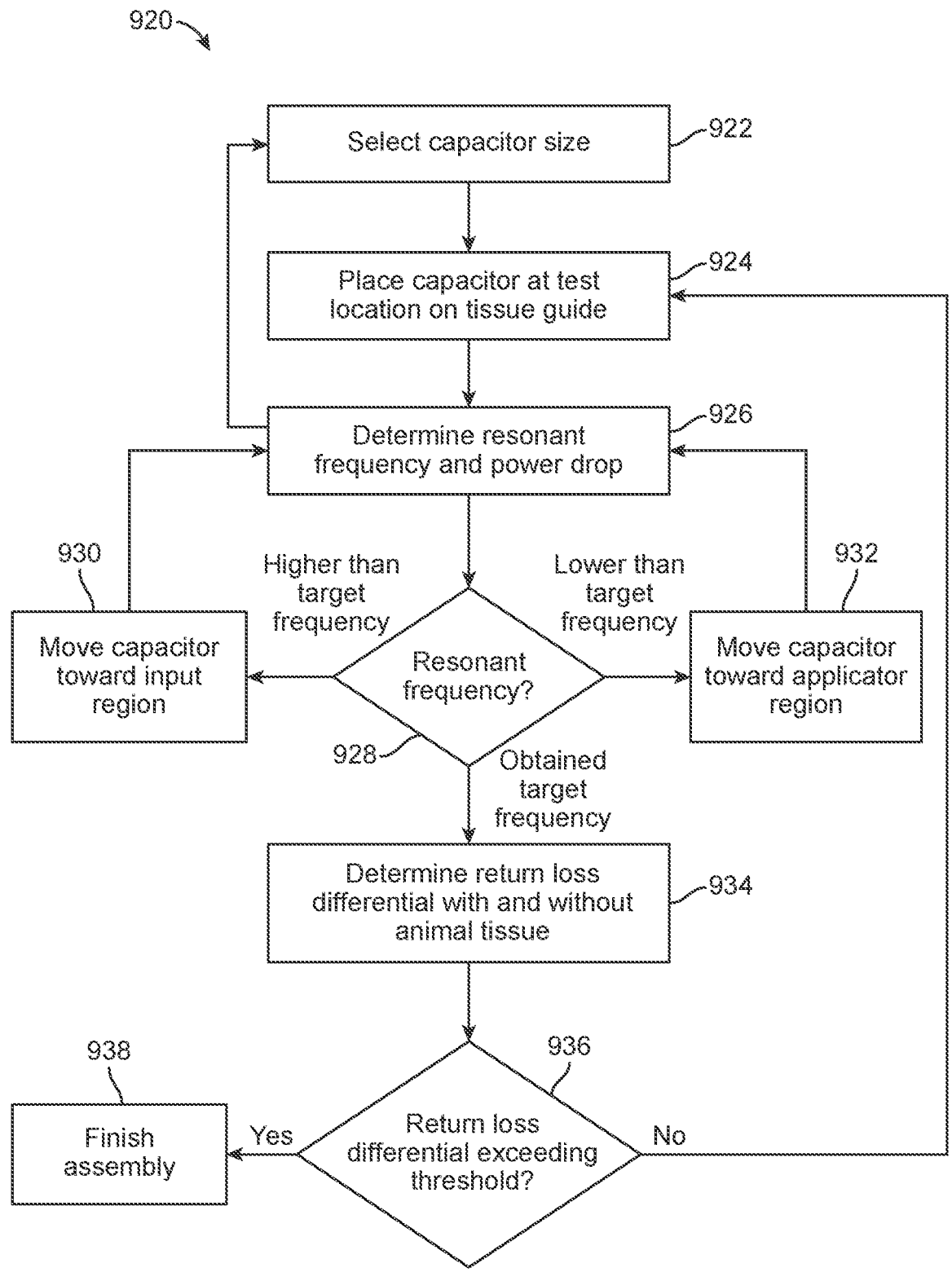
FIG. 13 illustrates a flowchart of a method for tuning for use with the receptacle of FIGS. 2A and 12.

FIG. 13 shows a flowchart of one example of a method for tuning a receptacle of the present disclosure. Method 920 may be used to tune a tissue guide or receptacle, such as receptacle 202 (FIG. 12), to deliver RF energy at a target frequency to animal tissue. In general, the method includes adjusting a position of one or more capacitors along one or more conductors of a tuning board of the RF applicator to achieve a target resonant frequency. Each capacitor may be associated with one channel of the RF applicator.

Method 920 may include selecting an initial capacitor size 922. Previous empirical data may be used to determine an initial capacitor size. For example, some capacitor sizes may range from 3 to 30 picofarads (pF).

The selected capacitor may be placed at a test location on the tuning board of the tissue guide 924 in method 920. Previous empirical data may be used to determine an initial test location. The capacitor may be placed and operably coupled, for example, by soldering the capacitor between the respective conductor and the ground plane at the test location. Placing the capacitor may allow the capacitor to be electrically and mechanically coupled to one or more conductors at the test location.

Once the selected capacitor is placed, method 920 may include determining a resonant frequency of one or more channels on the tuning board and a corresponding power drop 926. Any suitable technique to determine the resonant frequency may be used that is known to one skilled in the art having the benefit of this disclosure. In one example, the one or more channels may be analyzed using an RF vector network analyzer (VNA).

The electromagnetically shielding housing, or cover, of the tissue guide may be placed to cover the tuning board while the resonant frequency is determined. The housing may affect the characteristics of the tuning board.

A target frequency during tuning may be set a particular amount higher than a nominal frequency of a coupled RF interface board, such as RF interface board 104 (FIG. 1), when tuning is performed without tissue in the processing position. The higher target frequency may facilitate a resonant frequency that is equal or substantially equal to the nominal frequency of the coupled RF interface board when tissue is placed in the processing position. In some embodiments, the target frequency may be set from 1.5 to 2% higher than the nominal frequency of the RF interface board. For example, if the RF interface board 104 has an RF frequency centered at 2.45 GHz, then the target frequency may be about 2.49 GHz. The target frequency may be defined as the desired resonant frequency when the tissue guide is fully assembled (e.g., including electromagnetic shielding) without animal tissue present near the applicator.

Resonant frequency is generally a function of capacitor size and location along the conductor. In some embodiments, the resonant frequency may not be able to be determined by method 920, for example, when the resonant frequency is outside of a desired range. In such cases, method 920 may return to selecting a new capacitor size 922 and placing the new capacitor at the test location 924.

Method 920 may also include evaluating or analyzing the resonant frequency 928. The capacitor may need to be moved, or repositioned to a different position, until the resonant frequency reaches the target frequency.

Method 920 may include moving the capacitor toward the input region 930 or to a position closer to the connector side, for example, in response to the resonant frequency being higher than the target frequency. Moving the capacitor toward the input region may lower the resonant frequency. The capacitor may be re-soldered at the new position.

Method 920 may also include moving 932 the capacitor toward the applicator region 906 or to a position closer to the applicator region 906, for example, in response to the resonant frequency being lower than the target frequency. Moving the capacitor toward the applicator region may raise the resonant frequency. The capacitor may be re-soldered at the new position.

Method 920 may include determining the return loss differential with, and without, animal tissue placed in the tissue guide 934. For example, a poultry toe may be positioned to receive RF energy in the tissue guide, and a return loss in decibels may be measured. The measured return loss may be compared to measuring a return loss in decibels when the bird's toe is not positioned to receive RF energy in the tissue guide.

Method 920 may include determining whether the return loss differential is greater than a predetermined threshold 936. The predetermined threshold may correspond to a desired difference between low-power and high-power RF energy. For example, the predetermined threshold may be equal to 15 decibels.

In some embodiments, in response to the return loss differential not exceeding the predetermined threshold, method 920 may return to selecting a new capacitor size 922 and placing the new capacitor at the test location 924. If the return loss differential is less than the threshold, the tissue guide may not be sufficiently sensitive. Sensitivity may be affected by the shape of a curve (e.g., wide and flat versus narrow and tall) that represents the return loss differential versus frequency. For example, a wide and flat curve may result in lower sensitivity, and a narrow and tall curve may result in higher sensitivity.

In response to the return loss differential exceeding the predetermined threshold, method 920 may proceed to finish assembly of the tissue guide 938. All the channels may be tuned before finally fastening the housing to cover the tuning board.

While the present disclosure is not so limited, an appreciation of various aspects of the disclosure will be gained through a discussion of the specific illustrative embodiments provided below. Various modifications of the illustrative embodiments, as well as additional embodiments of the disclosure, will become apparent herein.

Illustrative Embodiments

In embodiment A1, an energy delivery system comprises an RF synthesizer circuit configured to generate an RF electric signal and a preamplification stage operably coupled to an output of the RF synthesizer circuit. The preamplification stage comprises an attenuator. The system also comprises a board controller operably coupled to the attenuator of the preamplification stage. The board controller is configured to modify a gain setting of the attenuator. The system also comprises an output connection configured to provide a low-power signal or a high-power signal based on at least the RF electric signal and the gain setting of the attenuator. The low-power signal or the high-power signal is configured to be provided to an RF applicator configured to couple an alternating RF electric field to animal tissue.

In embodiment A2, a system comprises the system according to any A embodiment, further comprising at least one amplifier operably coupled between the attenuator and the output connection.

In embodiment A3, a system comprises the system according to any A embodiment, further comprising a circulator operably coupled between the preamplification stage and the output connection.

In embodiment A4, a system comprises the system according to any A embodiment, further comprising sensing circuitry configured to detect a power value corresponding to either the low-power signal or the high-power signal.

In embodiment A5, a system comprises the system according to any A embodiment, further comprising the RF applicator, wherein the RF applicator is operably coupled to the output connection.

In embodiment A6, a system comprises the system according to any A embodiment, wherein the RF applicator is coupled to a receptacle configured to guide animal tissue to a processing position for coupling with the alternating RF electric field.

In embodiment A7, a system comprises the system according to any A embodiment, wherein the receptacle is configured to guide a poultry claw into a processing position proximate to the RF applicator.

In embodiment A8, a system comprises the system according to any A embodiment, wherein the board controller is configured to provide a first gain setting of the attenuator to provide the low-power signal at the output connection and measuring a baseline return loss value corresponding to no animal tissue in a processing position of the RF applicator. The board controller is also configured to provide a second gain setting of the attenuator having a lower magnitude than a magnitude of the first gain setting to provide the high-power signal at the output connection in response to detecting a return loss value exceeding a loss threshold value. A return loss value exceeding the loss threshold value corresponds to animal tissue in the processing position of the RF applicator.

In embodiment A9, a system comprises the system according to any A embodiment, wherein the board controller is configured to enter a high-power tracking mode to modify a frequency of the RF electric signal when the high-power signal is provided at the output connection to impedance match to animal tissue.

In embodiment A10, a system comprises the system according to any A embodiment, wherein the preamplification stage is a first preamplification stage, further comprising a second preamplification stage operably coupled between the first preamplification stage and the output connection, wherein when switching between the low-power signal and the high-power signal, the board controller is configured to modify a gain setting of the second preamplification stage before modifying a gain setting of the first preamplification stage.

In embodiment A11, a system comprises the system according to any A embodiment, wherein when switching between the low-power signal and the high-power signal, the board controller is configured to modify the gain setting of the attenuator without modifying a gain value of an amplifier in the preamplification stage.

In embodiment A12, a system comprises the system according to any A embodiment, further comprising a housing configured to form an electromagnetic shield around at least a power sensor of the board controller.

In embodiment B1, a method of delivering energy to animal tissue comprises synthesizing an RF electric signal; adjusting attenuation of the RF electric signal to selectively provide a low-power signal or a high-power signal; and generating an alternating RF electric field from an RF applicator based on the low-power signal or the high-power signal to couple the alternating RF electric field to animal tissue.

In embodiment B2, a method comprises the method according to any B embodiment, further comprising adjusting a position of one or more tuning components along one or more conductors of a tuning board of the RF applicator to achieve a target resonant frequency, wherein each tuning component is associated with one channel of the RF applicator.

In embodiment C, a system comprises the system according to any A embodiment configured to perform the method according to any B embodiment.

In embodiment D1, an energy delivery system comprises an RF synthesizer circuit configured to generate an RF electric signal. The system also comprises a preamplification stage operably coupled to an output of the RF synthesizer circuit. The preamplification stage comprises an attenuator. The system also comprises a board controller operably coupled to the attenuator of the preamplification stage. The board controller is configured to modify a gain setting of the attenuator. The system further comprises an output connection configured to provide a low-power signal or a high-power signal based on at least the RF electric signal and the gain setting of the attenuator. The low-power signal or the high-power signal is configured to be provided to an RF applicator configured to couple an alternating RF electric field to animal tissue. A power ratio between the high-power signal and the low-power signal is at least 10 dBm.

In embodiment D2, a system comprises the system according to any D embodiment, further comprising at least one amplifier operably coupled between the attenuator and the output connection.

In embodiment D3, a system comprises the system according to any D embodiment, further comprising sensing circuitry configured to detect a power value corresponding to either the low-power signal or the high-power signal.

In embodiment D4, a system comprises the system according to embodiment D3, wherein the sensing circuitry comprises a forward sensing circuit configured to measure a forward power value and a reverse sensing circuit configured to measure a reflected power value.

In embodiment D5, a system comprises the system according to any D embodiment, further comprising the RF applicator, wherein the RF applicator is operably coupled to the output connection.

In embodiment D6, a system comprises the system according to any D embodiment, wherein the RF applicator is coupled to a receptacle configured to guide animal tissue to a processing position for coupling with the alternating RF electric field.

In embodiment D7, a system comprises the system according to embodiment D6, wherein the receptacle is configured to guide a poultry claw into the processing position proximate to the RF applicator.

In embodiment D8, a system comprises the system according to any D embodiment, wherein the board controller is configured to enter a detection mode to detect a change in return loss of the low-power signal.

In embodiment D9, a system comprises the system according to embodiment D8, wherein the board controller is configured to provide a first gain setting of the attenuator to provide the low-power signal at the output connection and measuring a baseline return loss value corresponding to no animal tissue in a processing position of the RF applicator. The board controller is also configured to provide a second gain setting of the attenuator having a lower magnitude than a magnitude of the first gain setting to provide the high-power signal at the output connection in response to detecting a return loss value exceeding a loss threshold value. A return loss value exceeding the loss threshold value corresponds to animal tissue in the processing position of the RF applicator.

In embodiment D10, a system comprises the system according to embodiment D9, wherein the loss threshold value is at least 2 dBm greater than the baseline return loss value and the board controller is optionally configured to correct for signal drift.

In embodiment D11, a system comprises the system according to any D embodiment, wherein the board controller is configured to enter a high-power tracking mode to modify a frequency of the RF electric signal when the high-power signal is provided at the output connection to impedance match the animal tissue.

In embodiment D12, a system comprises the system according to any D embodiment, wherein the preamplification stage is a first preamplification stage. The system further comprises a second preamplification stage operably coupled between the first preamplification stage and the output connection. When switching between the low-power signal and the high-power signal, the board controller is configured to modify a gain setting of the second preamplification stage before modifying a gain setting of the first preamplification stage.

In embodiment D13, a system comprises the system according to any D embodiment, wherein when switching between the low-power signal and the high-power signal, the board controller is configured to modify the gain setting of the attenuator without modifying a gain value of an amplifier in the preamplification stage.

In embodiment D14, a system comprises the system according to any D embodiment, further comprising a system controller operably coupled to the board controller. The system controller is further configured to provide at least one of a constant power output command and a high-power tracking command to the board controller.

In embodiment D15, a system comprises the system according to any D embodiment, wherein the power ratio of the high-power signal to the low-power signal is at least 10 dB.

In embodiment D16, a system comprises the system according to any D embodiment, wherein the RF electric signal has frequency content corresponding to at least one ISM frequency band.

In embodiment E1, an energy delivery system comprises a substrate having a first major surface and a second major surface opposite to the first major surface. The system also comprises an RF synthesizer circuit on the substrate configured to generate an RF electric signal. The system further comprises an output connection on the substrate configured to provide a low-power signal or a high-power signal to an RF applicator to couple an alternating RF electric field to animal tissue. The system further comprises a preamplification stage on the first major surface of the substrate operably coupled between the RF synthesizer circuit and the output connection. The system further comprises a board controller on the substrate operably coupled to the preamplification stage and configured to adjust a gain setting for the preamplification stage. The system also comprises a circulator on the substrate operably coupled between the preamplification stage and the output connection. In addition, the system comprises power sensing circuitry. The power sensing circuitry comprises a directional coupler on the first major surface of the substrate operably coupled to a port of the circulator; and a power sensor on the second major surface of the substrate operably coupled to the directional coupler and the board controller.

In embodiment E2, a system comprises the system according to any E embodiment, wherein the power sensing circuitry comprises a forward power sensing circuit and a reverse sensing circuit. Each circuit is operably coupled to a different port of the circulator.

In embodiment E3, a system comprises the system according to any E embodiment, further comprising a housing coupled to the substrate configured to form an electromagnetic shield around at least the power sensor.

In embodiment F1, a method of delivering energy to animal tissue comprises synthesizing an RF electric signal. The method also comprises adjusting attenuation of the RF electric signal to selectively provide a low-power signal or a high-power signal. The method further comprises generating an alternating RF electric field from an RF applicator based on the low-power signal or the high-power signal to couple the alternating RF electric field to animal tissue. A power ratio between the high-power signal and the low-power signal may be at least 10 dBm.

In embodiment F2, a method comprises the method according to any F embodiment, further comprising positioning animal tissue in a processing position for coupling with the alternating RF electric field.

In embodiment F3, a method comprises the method according to any F embodiment, further comprising amplifying the attenuated RF electric signal.

In embodiment F4, a method comprises the method according to any F embodiment, further comprising determining a return loss value in response to providing the low-power signal or high-power signal to the RF applicator.

In embodiment F5, a method comprises the method according to any F embodiment, further comprising providing the low-power signal to the RF applicator to sense whether animal tissue is in a processing position to couple to the alternating RF electric field.

In embodiment F6, a method comprises the method according to any F embodiment, further comprising providing the high-power signal to the RF applicator in response to detecting animal tissue in the processing position.

Thus, various embodiments of the ENERGY DELIVERY SYSTEM USING AN ELECTRIC FIELD are disclosed. Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

All references and publications cited herein are expressly incorporated herein by reference in their entirety into this disclosure, except to the extent they may directly contradict this disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a controller may be operably coupled to a DAC to provide data for conversion into an analog signal).

Terms related to orientation, such as "top" and "bottom," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

As used in this specification and the appended claims, the singular forms "a," "an," and "the" encompass embodiments having plural referents, unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

The phrases "at least one of," "comprises at least one of," and "one or more of" followed by a list refers to any one of the items in the list and any combination of two or more items in the list.

What is claimed is:

1. An energy delivery system, comprising:
    an RF synthesizer circuit configured to generate an RF electric signal at more than one frequency;
    a preamplification stage operably coupled to an output of the RF synthesizer circuit, wherein the preamplification stage comprises an attenuator;
    a board controller operably coupled to the RF synthesizer circuit and to the attenuator of the preamplification stage, wherein the board controller is configured to:
        modify a gain setting of the attenuator; and
        change the frequency of the RF electric signal to impedance match based on a return loss value;
    an output connection configured to provide a low-power signal or a high-power signal based on at least the RF electric signal and the gain setting of the attenuator; and
    an RF applicator operably coupled to the output connection, wherein the low-power signal or the high-power signal is configured to be provided to the RF applicator and the RF applicator is configured to couple an alternating low-power or high-power RF electric field to animal tissue for respectively sensing the presence of, or processing, the animal tissue;
    wherein the board controller is configured to:
        provide a first gain setting of the attenuator to provide the low-power signal at the output connection and measure a baseline return loss value corresponding to no animal tissue in a processing position of the RF applicator; and
        provide a second gain setting of the attenuator having a lower magnitude than a magnitude of the first gain setting to provide the high-power signal at the output connection in response to detecting a return loss value exceeding a loss threshold value, wherein a return loss value exceeding the loss threshold value corresponds to animal tissue in the processing position of the RF applicator.

2. The system according to claim 1, further comprising at least one amplifier operably coupled between the attenuator and the output connection.

3. The system according to claim 1, further comprising a circulator operably coupled between the preamplification stage and the output connection.

4. The system according to claim 1, further comprising sensing circuitry configured to detect a power value corresponding to either the low-power signal or the high-power signal.

5. The system according to claim 1, wherein the RF applicator is coupled to a receptacle configured to guide animal tissue to a processing position for coupling with the alternating RF electric field.

6. The system according to claim 5, wherein the receptacle is configured to guide a poultry claw into a processing position proximate to the RF applicator.

7. The system according to claim 1, wherein the board controller is configured to enter a high-power tracking mode to modify a frequency of the RF electric signal when the high-power signal is provided at the output connection to impedance match to animal tissue.

8. The system according to claim 1, further comprising one or more preamplification stages including the preamplification stage, the one or more preamplification stages comprising the attenuator, another attenuator, and an amplifier having a fixed amplification value operably coupled between the attenuator and the another attenuator.

9. The system according to claim 1, wherein the preamplification stage is a first preamplification stage, further comprising a second preamplification stage operably coupled between the first preamplification stage and the output connection, wherein when switching between the low-power signal and the high-power signal, the board controller is configured to modify a gain setting of the second preamplification stage before modifying a gain setting of the first preamplification stage.

10. The system according to claim 1, wherein when switching between the low-power signal and the high-power signal, the board controller is configured to modify a gain setting of the preamplification stage without modifying a gain value of an amplifier in the preamplification stage.

11. The system according to claim 1, further comprising a housing configured to form an electromagnetic shield around at least a power sensor of the board controller.

12. A method of delivering energy to animal tissue, comprising:
synthesizing an RF electric signal;
adjusting attenuation of the RF electric signal to selectively provide a low-power signal or a high-power signal; and
generating an alternating RF electric field from an RF applicator based on the low-power signal or the high-power signal to couple a low-power or high-power alternating RF electric field to animal tissue for respectively sensing the presence of, or processing, the animal tissue;
wherein adjusting attenuation of the RF electrical signal comprises:
providing a first gain setting to provide the low-power signal and measuring a baseline return loss value corresponding to no animal tissue in a processing position of the RF applicator; and
providing a second gain setting having a lower magnitude than a magnitude of the first gain setting to provide the high-power signal in response to detecting a return loss value exceeding a loss threshold value, wherein a return loss value exceeding the loss threshold value corresponds to animal tissue in the processing position of the RF applicator.

13. The method according to claim 12, further comprising adjusting a position of one or more tuning components along one or more conductors of a tuning board of the RF applicator to achieve a target resonant frequency, wherein each tuning component is associated with one channel of the RF applicator.

14. The method of claim 12, comprising entering a high-power tracking mode to modify a frequency of the RF electric signal when the high-power signal is provided to impedance match to animal tissue.

15. The method of claim 12, wherein:
adjusting attenuation of the RF electric signal comprises adjusting the attenuation via a first preamplification stage and a second preamplification stage; and
the method comprises switching between the low-power signal and the high-power signal, wherein the switching comprises modifying a gain setting of the second preamplification stage before modifying a gain setting of the first preamplification stage.

16. The method of claim 15, wherein when switching between the low-power signal and the high-power signal, the method comprises modifying the gain setting without modifying a gain value of an amplifier in the first and second preamplification stages.

17. The method of claim 12, comprising detecting a power value corresponding to either the low-power signal or the high-power signal.

18. The method of claim 12, wherein the RF applicator is coupled to a receptacle configured to guide animal tissue to a processing position for coupling with the alternating RF electric field.

19. The method of claim 18, wherein the receptacle is configured to guide a poultry claw into a processing position proximate to the RF applicator.

20. An energy delivery system, comprising:
an RF synthesizer circuit configured to generate an RF electric signal at more than one frequency;
a preamplification stage operably coupled to an output of the RF synthesizer circuit, wherein the preamplification stage comprises an attenuator;
a board controller operably coupled to the RF synthesizer circuit and to the attenuator of the preamplification stage, wherein the board controller is configured to:
modify a gain setting of the attenuator; and
change the frequency of the RF electric signal to impedance match based on a return loss value;
an output connection configured to provide a low-power signal or a high-power signal based on at least the RF electric signal and the gain setting of the attenuator; and
an RF applicator operably coupled to the output connection, wherein the low-power signal or the high-power signal is configured to be provided to the RF applicator and the RF applicator is configured to couple an alternating low-power or high-power RF electric field to animal tissue for respectively sensing the presence of, or processing, the animal tissue
wherein when switching between the low-power signal and the high-power signal, the board controller is configured to modify a gain setting of the preamplification stage without modifying a gain value of an amplifier in the preamplification stage.

21. The system according to claim 20, further comprising at least one amplifier operably coupled between the attenuator and the output connection.

22. The system according to claim 20, further comprising a circulator operably coupled between the preamplification stage and the output connection.

23. The system according to claim 20, further comprising sensing circuitry configured to detect a power value corresponding to either the low-power signal or the high-power signal.

24. The system according to claim 20, wherein the RF applicator is coupled to a receptacle configured to guide animal tissue to a processing position for coupling with the alternating RF electric field.

25. The system according to claim 24, wherein the receptacle is configured to guide a poultry claw into a processing position proximate to the RF applicator.

26. The system according to claim 20, wherein the board controller is configured to enter a high-power tracking mode to modify a frequency of the RF electric signal when the high-power signal is provided at the output connection to impedance match to animal tissue.

27. The system according to claim 20, further comprising one or more preamplification stages including the preamplification stage, the one or more preamplification stages comprising the attenuator, another attenuator, and an amplifier having a fixed amplification value operably coupled between the attenuator and the another attenuator.

28. The system according to claim 20, wherein the preamplification stage is a first preamplification stage, further comprising a second preamplification stage operably coupled between the first preamplification stage and the output connection, wherein when switching between the low-power signal and the high-power signal, the board controller is configured to modify a gain setting of the second preamplification stage before modifying a gain setting of the first preamplification stage.

29. The system according to claim 20, further comprising a housing configured to form an electromagnetic shield around at least a power sensor of the board controller.

* * * * *